United States Patent
Garrison

(10) Patent No.: US 12,280,216 B2
(45) Date of Patent: Apr. 22, 2025

(54) MIXTURES INCLUDING NITROUS OXIDE

(71) Applicant: Thomas E. Garrison, Scottsdale, AZ (US)

(72) Inventor: Thomas E. Garrison, Scottsdale, AZ (US)

( * ) Notice: Subject to any disclaimer, the term of this patent is extended or adjusted under 35 U.S.C. 154(b) by 0 days.

(21) Appl. No.: 18/662,085

(22) Filed: May 13, 2024

(65) Prior Publication Data

US 2024/0299694 A1     Sep. 12, 2024

Related U.S. Application Data

(63) Continuation-in-part of application No. 18/104,540, filed on Feb. 1, 2023, now Pat. No. 11,980,717.

(51) Int. Cl.
    *A61M 16/12*      (2006.01)
    *A61M 16/06*      (2006.01)

(52) U.S. Cl.
    CPC ............ *A61M 16/12* (2013.01); *A61M 16/06* (2013.01); *A61M 2202/0283* (2013.01)

(58) Field of Classification Search
    CPC ........... C01B 21/22; A61M 2202/0283; A61M 16/104; A61M 16/12; A61M 16/009; A61M 16/0093; A61M 16/0891; A61M 16/06; A61M 11/04; A61M 11/041; A61M 11/042; A61M 11/02; A61M 11/005; Y02C 20/10
See application file for complete search history.

(56) References Cited

U.S. PATENT DOCUMENTS

| | | | |
|---|---|---|---|
| 6,221,377 B1 | 4/2001 | Meyer | |
| 9,757,528 B2 | 9/2017 | Rubin | |
| 11,065,223 B2 | 7/2021 | Rosenblatt et al. | |
| 11,273,274 B1 * | 3/2022 | Schatz | A61M 15/0085 |

(Continued)

FOREIGN PATENT DOCUMENTS

| | | |
|---|---|---|
| CN | 103127165 A | 6/2013 |
| WO | 2021138602 A1 | 7/2021 |
| WO | 2022069690 A2 | 4/2022 |

OTHER PUBLICATIONS

Kalmoe et al., "Ketamine and nitrous oxide: The evolution of NMDA receptor antagonists as antidepressant agents", Mar. 14, 2020, Elsevier, All Pages (Year: 2020).*

(Continued)

*Primary Examiner* — Joseph D. Boecker
*Assistant Examiner* — Brian T Khong
(74) *Attorney, Agent, or Firm* — Kunzler Bean & Adamson

(57) ABSTRACT

Apparatus for providing a mixture including nitrous oxide ($N_2O$) to a subject are disclosed. One apparatus includes a first reservoir for storing a first gas including at least $N_2O$ and a mask connected to the first reservoir in which the mask includes a second reservoir integrated with the mask. The second reservoir is for storing a first additive and the mask is for combining the first gas and the first additive to create a mixture including at least the $N_2O$ and the first additive in the mask and introducing the mixture to the mouth and/or nose of a subject. Another apparatus includes a configuration including separate first and second reservoirs storing at least $N_2O$ and a first additive in which the first reservoir and/or the second reservoir are detachably connected to the mask.

20 Claims, 11 Drawing Sheets

(56) References Cited

U.S. PATENT DOCUMENTS

| | | | |
|---|---|---|---|
| 2003/0127102 A1* | 7/2003 | Strawder | A61M 16/06 128/206.28 |
| 2008/0066741 A1 | 3/2008 | LeMahieu et al. | |
| 2008/0173558 A1* | 7/2008 | Arvanitis | A61M 15/085 128/202.13 |
| 2010/0163033 A1 | 7/2010 | Hyde et al. | |
| 2012/0045528 A1 | 2/2012 | Bessiere et al. | |
| 2019/0126096 A1 | 5/2019 | Squibb | |
| 2019/0328699 A1* | 10/2019 | Forde | A61M 16/14 |
| 2020/0197654 A1* | 6/2020 | Alizoti | A61M 11/04 |
| 2023/0001128 A1 | 1/2023 | Shuster et al. | |
| 2023/0285780 A1* | 9/2023 | Phillips-Reyes | A62B 18/003 |

OTHER PUBLICATIONS

J. Jarry, "This Sticky Pain Patch's Science Hits a Sticky Patch", Office for Science and Society (OSS), Sep. 23, 2022, pp. 1-7.

"Kailo Review: Targeted Pain Relief Patch Nanotech That Works—2021 Review", 2021Review.com, Mach 11, 2021, pp. 1-8.

M.C. Kalmoe et al., "Ketamine and nitrous oxide: The evolution of NMDA receptor antagonists as antidepressant agents", Journal of the Neurological Sciences, Mar. 19, 2020, pp. 1-8.

\* cited by examiner

MIXTURES INCLUDING NITROUS OXIDE

REFERENCE TO RELATED APPLICATION

This application claims priority to and is a continuation-in-part of U.S. patent application Ser. No. 18/104,540, now U.S. Pat. No. 11,980,717, filed on Feb. 1, 2023, the contents of which are incorporated herein by reference, in their entirety.

FIELD

The subject matter disclosed herein relates to nitrous oxide ($N_2O$) and, more particularly, relates to mixtures that include $N_2O$.

BACKGROUND

Nitrous oxide ($N_2O$) is used in medicine and dentistry and is often referred to as laughing gas. However, $N_2O$ is typically used singularly or alone, which can limit the usefulness of $N_2O$.

BRIEF SUMMARY

The subject matter of the present disclosure provides examples of mixtures that include nitrous oxide ($N_2O$) that can increase the usefulness of $N_2O$. Accordingly, the subject matter of the present application has been developed in response to the present state of the art, and in particular, in response to the limited uses of $N_2O$ and/or the limited uses of conventional apparatus (and/or systems) and methods that use $N_2O$.

Disclosed herein are apparatus for providing a mixture including nitrous oxide ($N_2O$) to a subject. One apparatus includes a first reservoir configured to store a first gas, the first gas including at least $N_2O$ and a mask coupled to the first reservoir in which the mask includes a second reservoir integrated with the mask. The second reservoir is configured to store a first additive and the mask is configured to combine the first gas and the first additive to create a mixture including at least the $N_2O$ and the first additive in the mask and introduce the mixture to one of a mouth of a subject, a nose of the subject, or both the mouth and the nose of the subject for inhalation by the subject. The preceding subject matter of this paragraph characterizes example 1 of the present disclosure.

The first additive comprises one of a liquid, a second gas, a compressed gas, or a combination thereof. The preceding subject matter of this paragraph characterizes example 2 of the present disclosure, wherein example 2 also includes the subject matter according to example 1, above.

The first gas comprises a first predetermined percentage of the $N_2O$ in the range of 0.1% to 100% by volume. The preceding subject matter of this paragraph characterizes example 3 of the present disclosure, wherein example 3 also includes the subject matter according to example 1, above.

The first gas further comprises a second predetermined percentage of a second additive in the range of 0.1% to 99.9% by volume. The preceding subject matter of this paragraph characterizes example 4 of the present disclosure, wherein example 4 also includes the subject matter according to any one of examples 1 or 3, above.

The mixture comprises a predetermined percentage of the $N_2O$ in the range of 20% to 99% by volume. The preceding subject matter of this paragraph characterizes example 5 of the present disclosure, wherein example 5 also includes the subject matter according to example 1, above.

The first gas further comprises one of compressed air, pure oxygen ($O_2$), air, or atmospheric air. The preceding subject matter of this paragraph characterizes example 6 of the present disclosure, wherein example 6 also includes the subject matter according to example 1, above.

The first additive comprises one of water ($H_2O$), hydrogen peroxide ($H_2O_2$), a *cannabis* extract, an essential oil, an herbal extract, a supplement, a medication, a vitamin, caffeine, a silver, a flavoring, a nano-capacitor, or a nutrient. The preceding subject matter of this paragraph characterizes example 7 of the present disclosure, wherein example 7 also includes the subject matter according to any one of examples 1 or 6, above.

The second reservoir is further configured to store a second additive and the second additive comprises a different one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient. The preceding subject matter of this paragraph characterizes example 8 of the present disclosure, wherein example 8 also includes the subject matter according to any one of examples 1, 6, or 7, above.

The first additive comprises one of $H_2O$, hydrogen peroxide $H_2O_2$, a *cannabis* extract, an essential oil, an herbal extract, a supplement, a medication, a vitamin, caffeine, a silver, a flavoring, a nano-capacitor, or a nutrient. The preceding subject matter of this paragraph characterizes example 9 of the present disclosure, wherein example 9 also includes the subject matter according to example 1, above.

The second reservoir is further configured to store a second additive and the second additive comprises a different one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient. The preceding subject matter of this paragraph characterizes example 10 of the present disclosure, wherein example 10 also includes the subject matter according to any one of examples 1 or 9, above.

Another apparatus includes a mask, a first reservoir storing a first gas including at least $N_2O$, and a second reservoir storing at least a first additive to the gas. The first reservoir and the second reservoir are separate reservoirs and at least one of the first reservoir and the second reservoir is detachably coupleable to the mask. The mask is configured to combine the first gas and the first additive to create a mixture including at least the $N_2O$ and the first additive in the mask and introduce the mixture to one of a mouth of a subject, a nose of the subject, or both the mouth and the nose of the subject for inhalation by the subject. The preceding subject matter of this paragraph characterizes example 11 of the present disclosure.

The first gas comprises a first predetermined percentage of the $N_2O$ in the range of 0.1% to 100% by volume. The preceding subject matter of this paragraph characterizes example 12 of the present disclosure, wherein example 12 also includes the subject matter according to example 11, above.

The first gas further comprises a second predetermined percentage of a second additive in the range of 0.1% to 99.9% by volume. The preceding subject matter of this paragraph characterizes example 13 of the present disclosure, wherein example 13 also includes the subject matter according to any one of examples 11 or 12, above.

The mixture comprises a predetermined percentage of the $N_2O$ in the range of 20% to 99% by volume. The preceding subject matter of this paragraph characterizes example 14 of the present disclosure, wherein example 14 also includes the subject matter according to example 11, above.

The first gas further comprises one of compressed air, $O_2$, air, or atmospheric air. The preceding subject matter of this paragraph characterizes example 15 of the present disclosure, wherein example 15 also includes the subject matter according to example 11, above.

The first additive comprises one of $H_2O$, $H_2O_2$, a *cannabis* extract, an essential oil, an herbal extract, a supplement, a medication, a vitamin, caffeine, a silver, a flavoring, a nano-capacitor, or a nutrient. The preceding subject matter of this paragraph characterizes example 16 of the present disclosure, wherein example 16 also includes the subject matter according to any one of examples 11 or 15, above.

The second reservoir is further configured to store a second additive and the second additive comprises a different one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient. The preceding subject matter of this paragraph characterizes example 17 of the present disclosure, wherein example 17 also includes the subject matter according to any one of examples 11, 15, or 16, above.

The first additive comprises one of $H_2O$, $H_2O_2$, a *cannabis* extract, an essential oil, an herbal extract, a supplement, a medication, a vitamin, caffeine, a silver, a flavoring, a nano-capacitor, or a nutrient. The preceding subject matter of this paragraph characterizes example 18 of the present disclosure, wherein example 18 also includes the subject matter according to example 11, above.

The second reservoir is further configured to store a second additive and the second additive comprises a different one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient. The preceding subject matter of this paragraph characterizes example 19 of the present disclosure, wherein example 19 also includes the subject matter according to any one of examples 11 or 18, above.

Both the first reservoir and the second reservoir are detachably coupleable to the mask. The preceding subject matter of this paragraph characterizes example 20 of the present disclosure, wherein example 20 also includes the subject matter according to example 11, above.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Various embodiments disclosed herein provide mixtures that include nitrous oxide ($N_2O$). Various other embodiments provide apparatus and methods that use $N_2O$.

It has been discovered that $N_2O$ is a non-competitive channel blocker of N-methyl-D-aspartate (NMDA) receptors and includes effects similar to the known NMDA receptor effects of Ketamine without the addictive shortcomings of Ketamine. That is, it has been discovered that inhaling a dose of $N_2O$ can produce a relatively rapid and relatively long-lasting anti-depressant effect, anti-anxiety effect on a subject with limited and/or reduced addictive consequences. Additionally, a dose of $N_2O$ may slow down the effects of Alzheimer's disease, memory loss, and/or brain damage. Further $N_2O$ can improve one or more symptoms of post-traumatic stress disorder (PTSD) by blocking induction and expression of behavioral sensitization by stress and/or blocking cross-sensitization between stress and stimulants. Further, $N_2O$ can positively affect the hyperactivity or hypofunction of the NMDA pathway and/or pathophysiology of a subject, which can at least decrease/reduce the effects of ischemic brain injury, chronic neurodegenerative diseases, pain, depression, and/or schizophrenia.

Additionally, Ketamine use for one or more of the indications discussed above is administered intravenously (IV), and excessive dosing of Ketamine can be fatal. As such, Ketamine is currently a schedule III drug controlled by the United States Food and Drug Administration and intravenous administration of Ketamine requires that medical personnel be immediately available to perform lifesaving resuscitation should such a need arise during administration. In other words, Ketamine is not self-administered, and self-administration is not allowed by the United States Food and Drug Administration.

In contrast, $N_2O$ is not a controlled substance and can be safely and effectively self-administered. Nitrous oxide can be inhaled and does not require IV administration. That is, $N_2O$ has a better safety profile than Ketamine and does not require medical supervision during administration. With the proper amount of oxygen, which can be provided as an additive, the potential of overdosing on $N_2O$ is at least significantly reduced, if not essentially eliminated. The methodology disclosed herein provides the medical benefits of the NMDA pathway of a subject via a safe delivery method of $N_2O$ that is appropriate for non-medical environments and self-administration.

Figure 1:
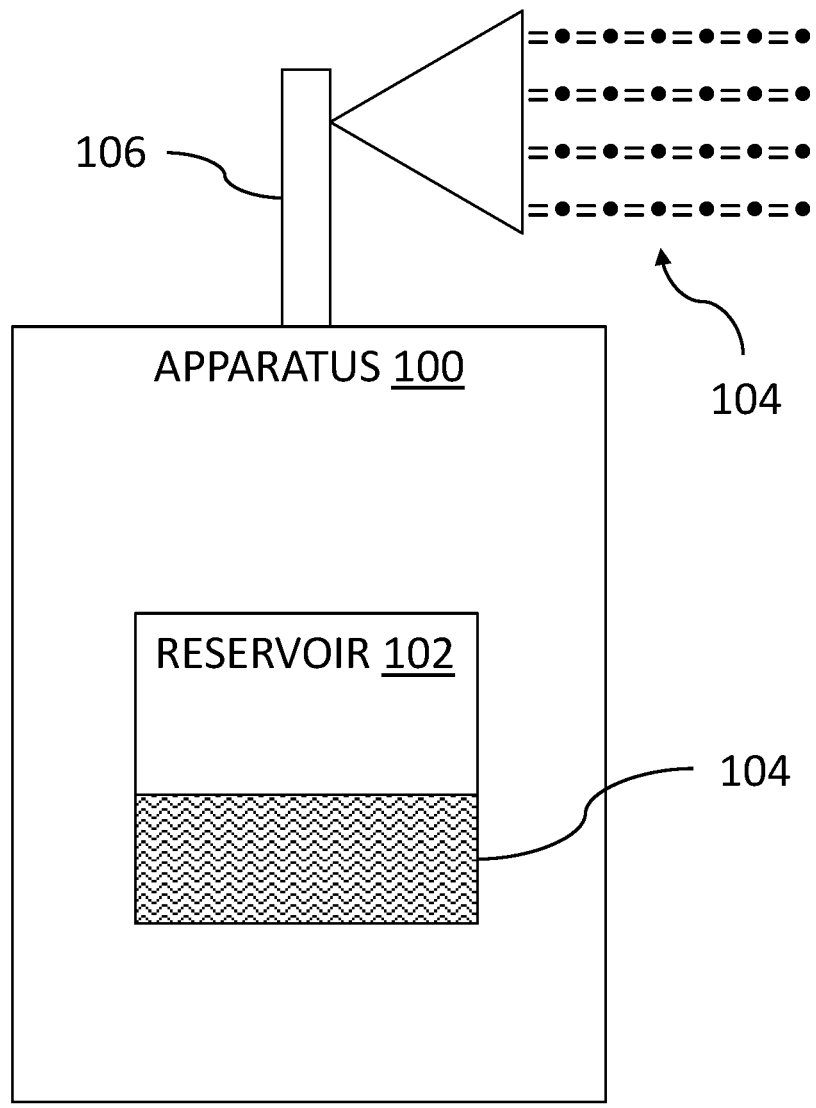
FIG. 1 is a schematic diagram of one embodiment of an apparatus including a reservoir that can provide a mixture including nitrous oxide ($N_2O$) to a subject/user.

With reference to the drawings, FIG. 1 is a diagram of one embodiment of an apparatus 100 that can provide a mixture including $N_2O$ to a subject (e.g., a human, an animal, etc.). The apparatus 100 may include any suitable device and/or system that is capable of introducing its contents (e.g., a mixture including $N_2O$) to the nose and/or mouth of a subject. Examples of an apparatus 100 include, but are not limited to, a nebulizer, an atomizer, an inhaler, a vaporizer, a humidifier, a mask, a mister, a fogger, and/or a sprayer, etc., among other devices and/or systems that are possible, each of which is contemplated herein.

At least in the exemplary embodiment shown in FIG. 1, the apparatus 100 includes, among other components, a reservoir 102 storing and/or capable of storing a mixture 104 and a delivery mechanism 106 in communication with the reservoir 102 and configured for introducing the mixture 104 to the nose and/or mouth of a subject. The reservoir 102 may include any suitable reservoir and/or type of reservoir that is known or developed in the future that is capable of storing and/or housing a mixture 104. In various embodiments, the reservoir 102 is capable of storing/housing the mixture 104 in the form of a liquid (e.g., a compressed liquid and/or a pressurized liquid) and/or a gas (e.g., a compressed gas and/or a pressurized gas).

The amount of the mixture 104 stored in the reservoir 102 may include any suitable amount of the mixture 104 that is capable of temporarily improving the psychological and/or mental health of a subject, as discussed in greater detail elsewhere herein. In some embodiments, the reservoir 102 includes a size that is capable of storing an amount of the mixture 104 defining a single dose and/or use of the mixture 104. In alternative embodiments, the reservoir 102 includes a size that is capable of storing an amount of the mixture 104 defining multiple (e.g., two or more) doses and/or uses of the mixture 104, which can include any suitable quantity of does/uses that is known or developed in the future.

The mixture 104, in various embodiments, includes $N_2O$. The amount and/or percentage of $N_2O$ in the mixture 104 may include any suitable amount and/or percentage of $N_2O$ that, subsequent to inhaling the mixture 104, is capable of at least temporarily improving the psychological and/or mental health of a subject, as discussed elsewhere herein.

In various embodiments, the mixture 104 includes at least twenty percent (20%) $N_2O$. As such, various embodiments of the mixture 104 can include an amount of $N_2O$ in the range of about 20% to about ninety-nine percent (99%) inclusive, among other amounts and/or percentages that are less than about 20% $N_2O$ or greater than about 99% $N_2O$ that are possible, each of which is contemplated herein.

The $N_2O$ in the mixture 104 may include any suitable form that is known or developed in the future. In various embodiments, the $N_2O$ in the mixture 104 may include $N_2O$ in liquid form (e.g., a compressed and/or pressurized) and/or in gas form (e.g., a compressed and/or pressurized). Further, it has been discovered that combining $N_2O$ with one or more additives to form a mixture 104 and inhaling such mixture 104 can provide additional benefits to a subject compared to $N_2O$ alone.

In further embodiments, the mixture 104 includes one or more additives combined with $N_2O$. The quantity of additives can include any suitable quantity of additives that is/are known or developed in the future. In some embodiments, the mixture 104 includes $N_2O$ combined with a single additive. In additional or alternative embodiments, the mixture 104 includes $N_2O$ combined with a plurality of additives (e.g., two (2) additives, three (3) additives, four (4) additives, five (5) additives, "n" additives, etc.).

An additive can include any suitable substance, liquid, and/or gas that can be suitably combined with $N_2O$ to form a mixture 104. Example additives can include, but are not limited to, air (e.g., pressurized air, compressed air, atmospheric air, etc.), pure oxygen ($O_2$), a *cannabis* extract, an essential oil, a silver and/or silver compound, an herb and/or herbal extract, a supplement, a medication, a vitamin, a nutrient, caffeine, a nano-capacitor, water ($H_2O$), hydrogen peroxide ($H_2O_2$), and/or a flavoring, etc., among other suitable additives that are possible, each of which is contemplated herein.

A *cannabis* extract can include any suitable substance that is known or developed in the future capable of being extracted from a *cannabis* plant (e.g., *Cannabis sativa*) that can be suitably combined with $N_2O$ to form a mixture 104. Example *cannabis* extracts can include, but are not limited to, a cannabidiol (CBD) extract and/or a tetrahydrocannabinol (THC) extract, etc., among other suitable extract from a *cannabis* plant that are possible, each of which is contemplated herein. In various embodiments, the mixture 104 includes $N_2O$ combined with one or more *cannabis* extracts or $N_2O$ combined with one or more *cannabis* extracts and one or more other additives.

An essential oil can include any suitable essential oil and/or combination of essential oils that is/are known or developed in the future that can be suitably combined with $N_2O$ to form a mixture 104. Example essential oils include, but are not limited to, lemon oil, peppermint oil, lavender oil, tee tree oil, eucalyptus oil, clove oil, chamomile oil, orange oil, spearmint oil, rosemary oil, grapefruit oil, oregano oil, ginger oil, lemongrass oil, spruce oil, pine oil, sandalwood oil, cedarwood oil, marjoram oil, clary sage oil, valerian oil, patchouli oil, vetiver oil, ylang ylang oil, frankincense oil, myrrh oil, neroli oil, and/or bergamot oil, among other suitable essential oils that are possible, each of which is contemplated herein. In various embodiments, the mixture 104 includes $N_2O$ combined with one or more essential oils or $N_2O$ combined with one or more essential oils and one or more other additives. A silver may include any suitable silver and/or silver compound that is known or developed in the future that can be suitably combined with $N_2O$ to form a mixture 104. Example silvers may include, but are not limited to, a colloidal silver, nano-silver, silver oxide ($Ag_2O$), etc., among other suitable silvers and/or silver compounds that are possible, each of which is contemplated herein. In some embodiments, a silver can include a colloidal silver and/or nano-silver manufactured by SilverCeuticals® LLC of Lindon, Utah. In various embodiments, the mixture 104 includes one or more silvers combined with at least $N_2O$.

An herb and/or herbal extract may include any suitable herb and/or extract from any suitable herb that is known or developed in the future that can be suitably combined with $N_2O$ to form a mixture 104. Example herbs and/or extracts from a herb can include, but are not limited to, echinacea, ginseng, Siberian, ginseng, *Ginkgo biloba*, elderberry, St. John's wort, turmeric, ginger, valerian, chamomile, mint, clover, henbane, mistletoe, monkshood, pasqueflower, primrose, vervain, garlic, saw palmetto, goldenseal, aloe, tulsi, amla, ashwagandha, gotu kola, neem, cumin, peppermint, and/or cinnamon, etc., among other herbs and/or herbal extracts that are possible, each of which is contemplated herein. In various embodiments, the mixture 104 includes one or more herbs and/or one or more herbal extracts combined with at least $N_2O$.

A supplement may include any suitable supplement that is known or developed in the future that can be suitably combined with $N_2O$ to form a mixture 104. Example supplements can include, but are not limited to, fish oil, a probiotic, Omega-3, curcumin, collagen, CoQ10, chondroitin, coconut oil, rose hips, melatonin, apple cider vinegar, green tea and/or green tea extract, cocoa and/or cocoa extract, and/or dark chocolate and/or dark chocolate extract, etc., among other supplements that are possible, each of which is contemplated herein. In various embodiments, the mixture 104 includes one or more supplements combined with at least $N_2O$.

A medication may include any suitable medication that is known or developed in the future that can be suitably combined with $N_2O$ to form a mixture 104. In various embodiments, a medication includes any medication that can be effectively absorbed through the lungs, without notably toxicity, and that can include a beneficial (perceived and/or substantiated) effect on the body of a subject (e.g., human, animal, etc.). Example medications can include, but are not limited to, a medication for asthma, chronic obstructive pulmonary disease (COPD), an infection, inflammation, cystic fibrosis, and/or an autoimmune disease, etc., among other medications that are possible, each of which is contemplated herein.

A vitamin may include any suitable vitamin or multivitamin that is known or developed in the future that can be suitably combined with $N_2O$ to form a mixture 104. Example vitamins include, but are not limited to, Vitamin A, Vitamin B (e.g., Vitamin B1 (Thiamine), Vitamin B2 (Riboflavin), Vitamin B3 (Niacin), Vitamin B5 (Pantothenic Acid), Vitamin B6 (Pyridoxine), Vitamin B7 (Biotin), Vitamin B9 (Folate or Folic Acid), Vitamin B12 (Cobalamin), a B-complex, etc.), Vitamin C (Ascorbic Acid), Vitamin D, Vitamin E, Vitamin K, and/or Choline, etc., among other vitamins and/or multivitamins that are possible, each of which is contemplated herein. In various embodiments, the mixture 104 includes one or more vitamins and/or a multivitamin combined with at least $N_2O$.

A nutrient may include any suitable nutrient and/or mineral that is known or developed in the future that can be suitably combined with $N_2O$ to form a mixture 104. Example nutrients include, but are not limited to, Calcium, Chloride, Chromium, Copper, Fluoride, Iodine, Iron, Magnesium, Manganese, Molybdenum, Phosphorus, Potassium, Selenium, Sodium, and/or Zinc, etc., among other nutrients and/or minerals that are possible, each of which is contemplated herein. In various embodiments, the mixture 104 includes one or more nutrients and/or minerals combined with at least $N_2O$.

A flavoring may include any suitable flavoring that is known or developed in the future that can be suitably combined with $N_2O$ to form a mixture 104. Example flavorings include, but are not limited to, a fruit flavoring (e.g., apple, strawberry, raspberry, pear, blackberry, blueberry, peach, plum, apricot, banana, pineapple, watermelon, grape, cherry, mango, papaya, kiwi, cantaloupe, orange, clementine, lemon, grapefruit, and/or lime, etc.), a mint flavoring (e.g., spearmint, peppermint, etc.), a chocolate flavoring, a coffee flavoring, and/or a vanilla flavoring, etc., among other flavorings that are possible, each of which is contemplated herein. In various embodiments, the mixture 104 includes one or more flavorings combined with at least $N_2O$.

A nano-capacitor may include any suitable nano-capacitor and/or type of nano-capacitor that is known or developed in the future. In some embodiments, the nano-capacitor includes a nano-capacitor manufactured by nCAP® Technologies LLC of Heber City, Utah.

The additive(s) in the mixture 104 may include any suitable form that is known or developed in the future. In various embodiments, the additive(s) in the mixture 104 may include one or more additives in a liquid form and/or one or more additives in a gas/gaseous form.

In various embodiments, the mixture 104 includes a minimum of about one percent (1%) of the one or more additives. As such, various embodiments of the mixture 104 can include an amount of the additive(s) in the range of about 1% to about eighty percent (80%) inclusive, among other amounts and/or percentages that are less than about 1% of the additive(s) or greater than about 80% of the additive(s) that are possible, each of which is contemplated herein.

In some embodiments, the $N_2O$ and the additive(s) make up the entirety (e.g., one hundred percent (100%)) or the substantial entirety of the mixture 104. In other embodiments, the $N_2O$ and the additive(s) make up less than 100% of the mixture 104.

A delivery mechanism 106 may include any suitable device and/or system that is capable of introducing a mixture 104 stored/housed in a reservoir 102 of an apparatus 100 to the nose and/or mouth of a subject. Examples of a delivery mechanism 106 can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 106 are configured to emit and/or expel the mixture 104 in the form of a spray, a fine spray, a mist, a stream, a vapor, an aerosol, a sprinkle, droplets, and/or a fog, etc., among other forms that are capable of being inhaled by a subject that are possible, each of which is contemplated herein.

Since the mixture 104 includes a combination of $N_2O$ and one or more additives, the delivery mechanism 106, in some embodiments, is configured to simultaneously deliver the $N_2O$ and the one or more additives to the mouth of a subject (e.g., a user) for inhalation by the subject/user. Similarly, since the mixture 104 includes a combination of $N_2O$ and one or more additives, the delivery mechanism 106, in some embodiments, is configured to simultaneously deliver the $N_2O$ and the one or more additives to the nose of a subject/user for inhalation by the subject/user. Similar still, since the mixture 104 includes a combination of $N_2O$ and one or more additives, the delivery mechanism 106, in some embodiments, is configured to simultaneously deliver the $N_2O$ and the one or more additives to both the mouth and the nose of a subject/user for inhalation by the subject/user.

FIGS. 2A through 2D are schematic diagrams of various embodiments of an apparatus 200A, 200B, 200C, and 200D that can provide a mixture 204A, 204B, 204C, and 204n, respectively (hereinafter referred to singularly and/or collectively simply as mixture(s) 204), including $N_2O$ to a subject and/or user similar to the apparatus 100 discussed with reference to FIG. 1. At least in the embodiment illustrated in FIG. 2A, the apparatus 200A includes, among other components, a reservoir 208 configured to store and/or storing $N_2O$ 210, a reservoir 212A configured to store and/or storing a first additive 214A, and a delivery mechanism 206A in communication with the reservoirs 208 and 212A and configured for introducing a mixture 204A to the nose and/or mouth of a subject.

A reservoir 208 may include any suitable reservoir and/or type of reservoir that is known or developed in the future that is capable of storing and/or housing an amount of $N_2O$ 210. In various embodiments, the reservoir 208 is capable of storing/housing the $N_2O$ 210 in the form of a compressed and/or pressurized liquid and/or a compressed and/or pressurized gas. As such, the $N_2O$ 210 stored in the reservoir 208 may be in the form of compressed liquid $N_2O$, pressurized liquid $N_2O$, compressed gaseous $N_2O$, and/or pressurized gaseous $N_2O$.

A reservoir 212A may include any suitable reservoir and/or type of reservoir that is known or developed in the future that is capable of storing and/or housing an amount of a first additive 214A. In various embodiments, the reservoir 212A is capable of storing/housing the first additive 214A in the form of a compressed and/or pressurized liquid and/or a compressed and/or pressurized gas. As such, the first additive 214A stored in the reservoir 212A may be in the form of a compressed liquid, a pressurized liquid, a compressed gas, and/or a pressurized gas.

The first additive 214A can include any suitable additive, substance, liquid, and/or gas that can be suitably combined with the $N_2O$ 210 to form a mixture 204A similar to at least one embodiment of the mixture 104 discussed above with reference to FIG. 1. For example, the first additive 214A may include, but is not limited to, air, pure oxygen, a *cannabis* extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206A may include any suitable device and/or system that is capable of introducing a mixture 204A including $N_2O$ 210 and the first additive 214A to the nose and/or mouth of a subject and/or user similar to the delivery mechanism 106 discussed above with reference to FIG. 1. Examples of a delivery mechanism 206A can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206A are configured to emit and/or expel the mixture 104 in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206A is configured to combine and/or facilitate combining the $N_2O$ 210 stored/housed in the reservoir 208 and the first additive 214A stored/housed in the reservoir 212A to generate and/or facilitate generating the mixture 204A. Since the mixture 204A includes a combination of the $N_2O$ 210 and the first additive 214A, the delivery mechanism 206A, in some embodiments, is configured to simultaneously deliver the $N_2O$ 210 and the first additive 214A to the mouth and/or nose of the subject and/or user for inhalation by the subject/user.

In various embodiments, the mixture 204A includes at least 20% of the $N_2O$ 210. That is, various embodiments of the mixture 204A can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204A, in various embodiments, includes a minimum of about 1% of the first additive 214A. That is, various embodiments of the mixture 204A can include an amount of the first additive 214A in the range of about 1% to about 80% inclusive, among other amounts and/or percentages that are less than about 1% of the first additive 214A or greater than about 80% of the first additive 214A that are possible, each of which is contemplated herein.

In some embodiments, the $N_2O$ 210 and the first additive 214A make up the entirety or substantially the entirety of the mixture 204A. In other embodiments, the $N_2O$ 210 and the first additive 214A make up less than 100% of the mixture 204A.

Figure 2A:
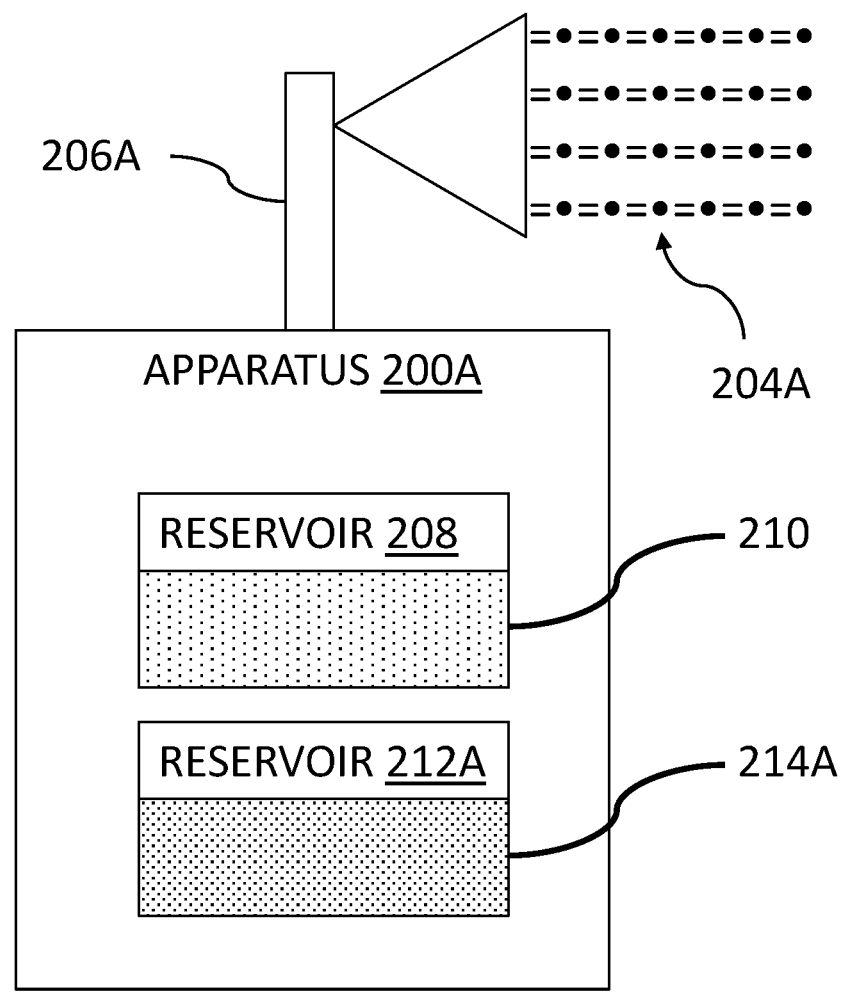
FIGS. 2A through 2D are schematic diagrams of various other embodiments of an apparatus that can provide a mixture including $N_2O$ to a subject/user.
Figure 2B:
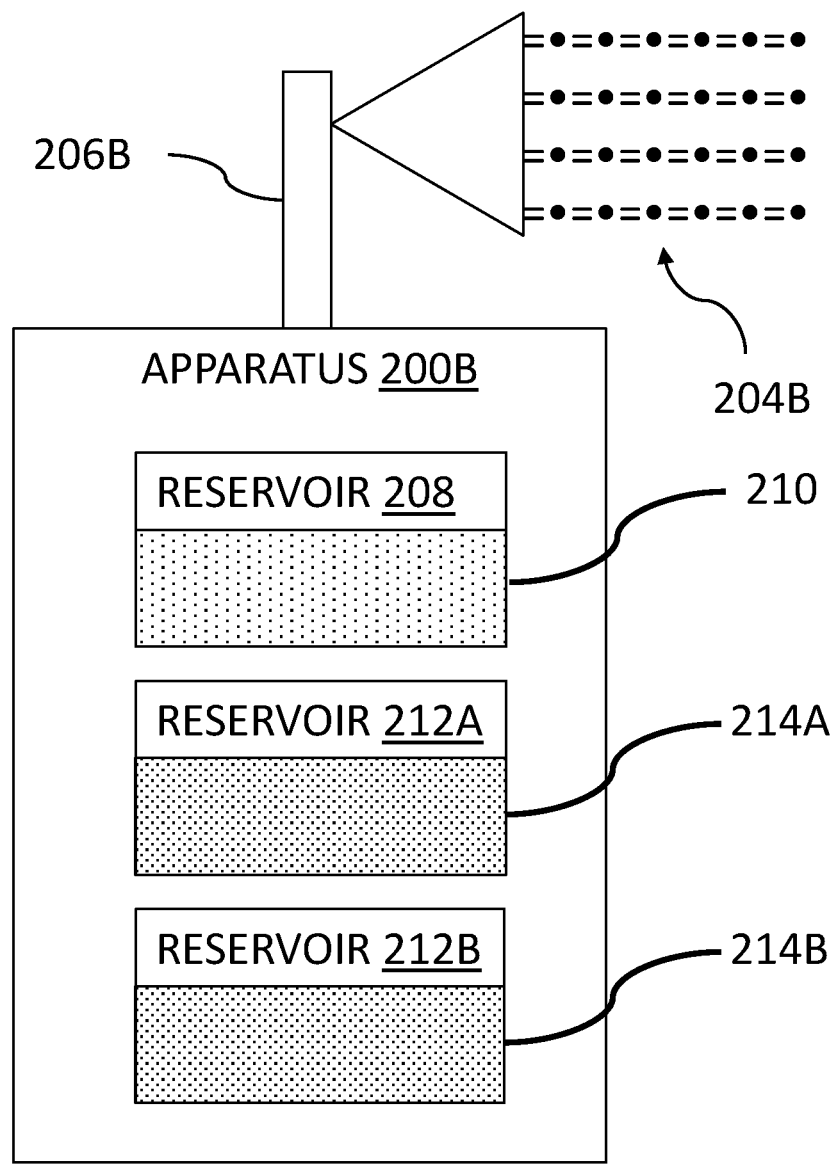

FIG. 2B illustrates another embodiment of an apparatus 200B similar to the apparatus 100 discussed with reference to FIG. 1 that can provide a mixture 204B including $N_2O$ to a subject and/or user. The apparatus 200B includes a reservoir 208 configured to store and/or storing $N_2O$ 210 and a reservoir 212A configured to store and/or storing a first additive 214A similar to various embodiments of the apparatus 200A discussed above with reference to FIG. 2A. At least in the embodiment illustrated in FIG. 2B, the apparatus 200B further includes, among other components, a reservoir 212B configured to store and/or storing a second additive 214B and a delivery mechanism 206B in communication with the reservoirs 208, 212A, and 212B and configured for introducing a mixture 204B to the nose and/or mouth of a subject.

A reservoir 212B may include any suitable reservoir and/or type of reservoir that is known or developed in the future that is capable of storing and/or housing an amount of a second additive 214B. In various embodiments, the reservoir 212B is capable of storing/housing the second additive 214B in the form of a compressed and/or pressurized liquid and/or a compressed and/or pressurized gas. As such, the second additive 214B stored in the reservoir 212B may be in the form of a compressed liquid, a pressurized liquid, a compressed gas, and/or a pressurized gas.

In some embodiments, the second additive 214B and the first additive 214A are the same additive and/or the same type of additive. In other embodiments, the second additive 214B and the first additive 214A are different additives and/or different types of additives.

The second additive 214B can include any suitable additive, substance, liquid, and/or gas that can be suitably combined with the $N_2O$ 210 (and the first additive 214A) to form a mixture 204B similar to at least one embodiment of the mixture 104 discussed above with reference to FIG. 1. For example, the second additive 214B may include, but is not limited to, air, pure oxygen, a *cannabis* extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206B may include any suitable device and/or system that is capable of introducing a mixture 204B including $N_2O$ 210, the first additive 214A, and the second additive 214B to the nose and/or mouth of a subject and/or user similar to the delivery mechanism 106 discussed above with reference to FIG. 1. Examples of a delivery mechanism 206B can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206B are configured to emit and/or expel the mixture 204B in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206B is configured to combine and/or facilitate combining the $N_2O$ 210 stored/housed in the reservoir 208, the first additive 214A stored/housed in the reservoir 212A, and the second additive 214B stored/housed in the reservoir 212B to generate and/or facilitate generating the mixture 204B. Since the mixture 204B includes a combination of the $N_2O$ 210, the first additive 214A, and the second additive 214B, the delivery mechanism 206B, in some embodiments, is configured to simultaneously deliver the $N_2O$ 210, the first additive 214A, and the second additive 214B to the mouth and/or nose of the subject and/or user for inhalation by the subject/user.

In various embodiments, the mixture 204B includes at least 20% of the $N_2O$ 210. That is, various embodiments of the mixture 204B can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204B, in various embodiments, includes a minimum of about 1% of the first additive 214A and the second additive 214B. That is, various embodiments of the mixture 204B can include an amount of the first additive 214A and the second additive 214B in the range of about 1% to about 80% inclusive, among other amounts and/or percentages that are less than about 1% of the first additive 214A and the second additive 214B or greater than about 80% of the first additive 214A and the second additive 214B that are possible, each of which is contemplated herein.

In some embodiments, the $N_2O$ 210, the first additive 214A, and the second additive 214B make up the entirety or substantially the entirety of the mixture 204B. In other embodiments, the $N_2O$ 210, the first additive 214A, and the second additive 214B make up less than 100% of the mixture 204B.

Figure 2C:
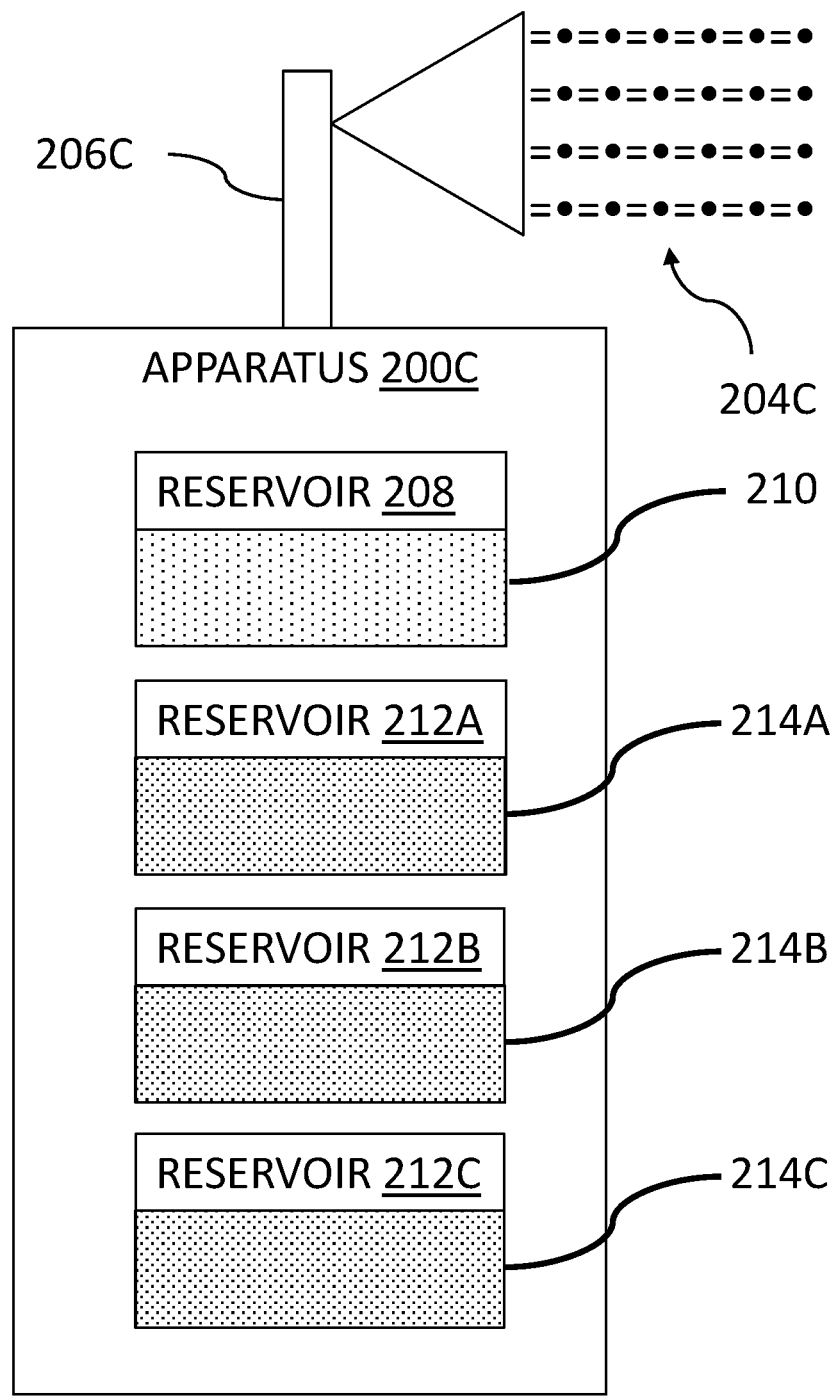

FIG. 2C illustrates a further embodiment of an apparatus 200C similar to the apparatus 100 discussed with reference to FIG. 1 that can provide a mixture 204C including $N_2O$ to a subject and/or user. The apparatus 200C includes a reservoir 208 configured to store and/or storing $N_2O$ 210, a reservoir 212A configured to store and/or storing a first additive 214A, and a reservoir 212B configured to store and/or storing a second additive 214B similar to various embodiments of the apparatus 200B discussed above with reference to FIG. 2B. At least in the embodiment illustrated in FIG. 2C, the apparatus 200C further includes, among other components, a reservoir 212C configured to store and/or storing a third additive 214C and a delivery mechanism 206C in communication with the reservoirs 208, 212A, 212B, and 212C and configured for introducing a mixture 204C to the nose and/or mouth of a subject.

A reservoir 212C may include any suitable reservoir and/or type of reservoir that is known or developed in the future that is capable of storing and/or housing an amount of a third additive 214C. In various embodiments, the reservoir 212C is capable of storing/housing the third additive 214C in the form of a compressed and/or pressurized liquid and/or a compressed and/or pressurized gas. As such, the third additive 214C stored in the reservoir 212C may be in the form of a compressed liquid, a pressurized liquid, a compressed gas, and/or a pressurized gas.

In some embodiments, the third additive 214C, the second additive 214B, and the first additive 214A are the same additive and/or the same type of additive. In other embodiments, at least two of the third additive 214C, the second additive 214B, and the first additive 214A are the same additive and/or the same type of additive. In still other embodiments, at least two of the third additive 214C, the second additive 214B, and the first additive 214A are different additives and/or different types of additives. In further embodiments, the third additive 214C, the second additive 214B, and the first additive 214A are different additives and/or different types of additives.

The third additive 214C can include any suitable additive, substance, liquid, and/or gas that can be suitably combined with the $N_2O$ 210 (and the first additive 214A and/or the second additive 214B) to form a mixture 204C similar to at least one embodiment of the mixture 104 discussed above with reference to FIG. 1. For example, the third additive 214C may include, but is not limited to, air, pure oxygen, a *cannabis* extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206C may include any suitable device and/or system that is capable of introducing a mixture 204C including $N_2O$ 210, the first additive 214A, the second additive 214B, and the third additive 214C to the nose and/or mouth of a subject and/or user similar to the delivery mechanism 106 discussed above with reference to FIG. 1. Examples of a delivery mechanism 206C can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206C are configured to emit and/or expel the mixture 204C in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206C is configured to combine and/or facilitate combining the $N_2O$ 210 stored/housed in the reservoir 208, the first additive 214A stored/housed in the reservoir 212A, the second additive 214B stored/housed in the reservoir 212B, and the third additive 214C stored/housed in the reservoir 212C to generate and/or facilitate generating the mixture 204C. Since the mixture 204C includes a combination of the $N_2O$ 210, the first additive 214A, the second additive 214B, and the third additive 214C, the delivery mechanism 206C, in some embodiments, is configured to simultaneously deliver the $N_2O$ 210, the first additive 214A, the second additive 214B, and the third additive 214C to the mouth and/or nose of the subject and/or user for inhalation by the subject/user.

In various embodiments, the mixture 204C includes at least 20% of the $N_2O$ 210. That is, various embodiments of the mixture 204C can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204C, in various embodiments, includes a minimum of about 1% of the first additive 214A, the second additive 214B, and the third additive 214C. That is, various embodiments of the mixture 204C can include an amount of the first additive 214A, the second additive 214B, and the third additive 214C in the range of about 1% to about 80% inclusive, among other amounts and/or percentages that are less than about 1% of the first additive 214A, the second additive 214B, and the third additive 214C or greater than about 80% of the first additive 214A, the second additive 214B, and the third additive 214C that are possible, each of which is contemplated herein.

In some embodiments, the $N_2O$ 210, the first additive 214A, the second additive 214B, and the third additive 214C make up the entirety or substantially the entirety of the mixture 204C. In other embodiments, the $N_2O$ 210, the first additive 214A, the second additive 214B, and the third additive 214C make up less than 100% of the mixture 204C.

Figure 2D:
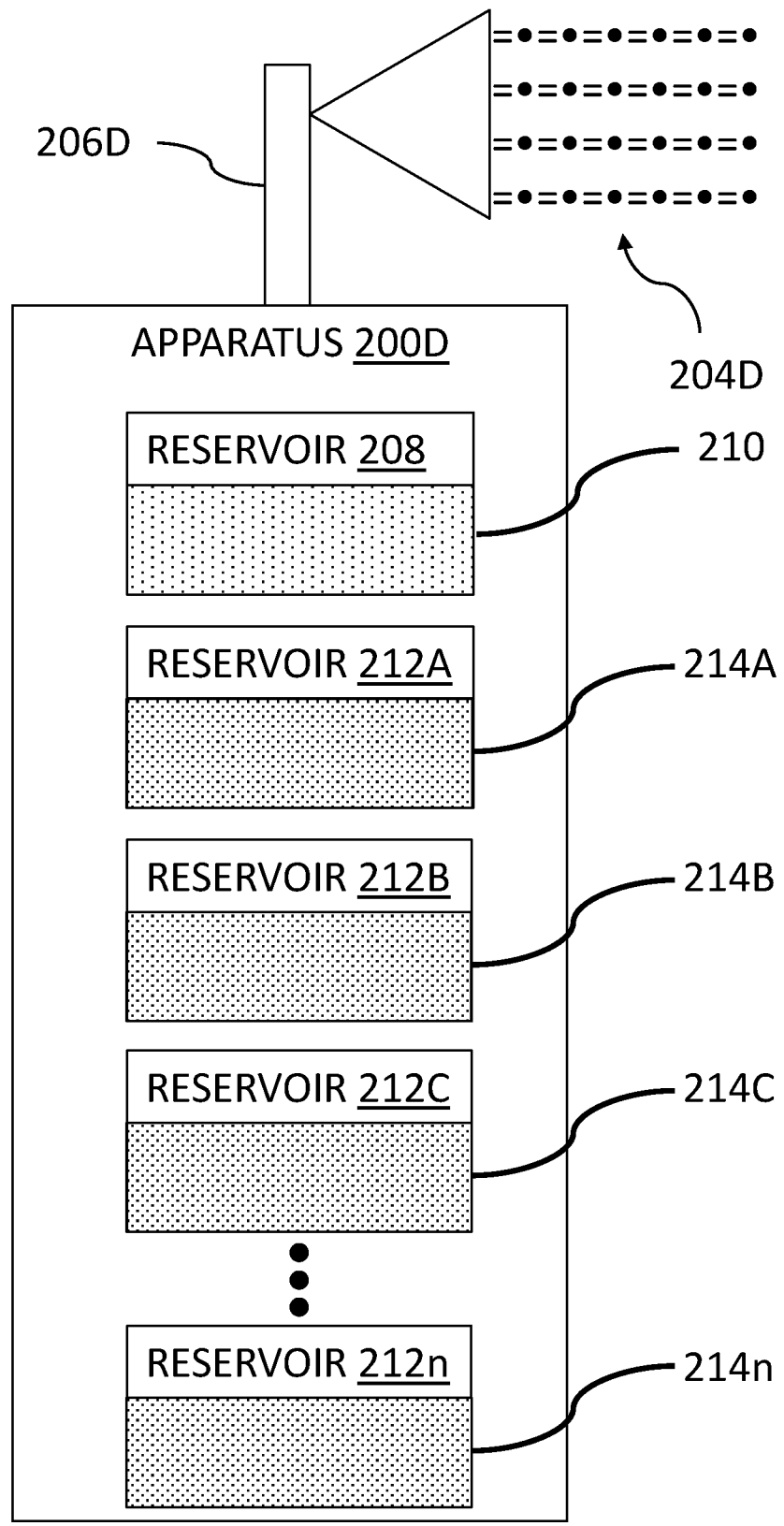

FIG. 2D illustrates a further embodiment of an apparatus 200D similar to the apparatus 100 discussed with reference to FIG. 1 that can provide a mixture 204D including $N_2O$ to a subject and/or user. The apparatus 200D includes a reservoir 208 configured to store and/or storing $N_2O$ 210, a reservoir 212A configured to store and/or storing a first additive 214A, a reservoir 212B configured to store and/or storing a second additive 214B, and a reservoir 212C configured to store and/or storing a third additive 214C similar to various embodiments of the apparatus 200C discussed above with reference to FIG. 2C. At least in the embodiment illustrated in FIG. 2D, the apparatus 200D further includes, among other components, at least one additional reservoir 212n configured to store and/or storing at least one additional additive 214n and a delivery mechanism 206D in communication with the reservoirs 208, 212A, 212B, 212C, and 212n and configured for introducing a mixture 204D to the nose and/or mouth of a subject.

A reservoir 212n may include any suitable reservoir and/or type of reservoir that is known or developed in the future that is capable of storing and/or housing an amount of a respective additional additive 214n. In various embodiments, the reservoir 212n is capable of storing/housing its respective additional additive 214n in the form of a compressed and/or pressurized liquid and/or a compressed and/or pressurized gas. As such, the additional additive 214n stored in the reservoir 212n may be in the form of a compressed liquid, a pressurized liquid, a compressed gas, and/or a pressurized gas.

In some embodiments, the additional additive 214n, the third additive 214C, the second additive 214B, and the first additive 214A are the same additive and/or the same type of additive. In other embodiments, at least two or three of the additional additive 214n, the third additive 214C, the second additive 214B, and the first additive 214A are the same additive and/or the same type of additive. In still other embodiments, at least two or three of the additional additive 214n, the third additive 214C, the second additive 214B, and the first additive 214A are different additives and/or different types of additives. In further embodiments, the additional additive 214n, the third additive 214C, the second additive 214B, and the first additive 214A are different additives and/or different types of additives.

The additional additive 214n can include any suitable additive, substance, liquid, and/or gas that can be suitably combined with the $N_2O$ 210 (and the first additive 214A, the second additive 214B, and/or the third additive 214C) to form a mixture 204D similar to at least one embodiment of the mixture 104 discussed above with reference to FIG. 1.

For example, the additional additive 214n may include, but is not limited to, air, pure oxygen, a *cannabis* extract, an essential oil, a silver and/or silver compound, an herb and/or herbal extract, a supplement, a medication, a vitamin, a nutrient, caffeine, a nano-capacitor, water, hydrogen peroxide, and/or a flavoring, etc., among other suitable additives that are possible, each of which is contemplated herein similar to the various embodiments of an additive in at least one embodiment of the mixture 104 discussed above with reference to FIG. 1.

A delivery mechanism 206D may include any suitable device and/or system that is capable of introducing a mixture 204D including $N_2O$ 210, the first additive 214A, the second additive 214B, the third additive 214C, and one or more additional additives 214n to the nose and/or mouth of a subject and/or user similar to the delivery mechanism 106 discussed above with reference to FIG. 1. Examples of a delivery mechanism 206D can include, but are not limited to, a nebulizer, an atomizer, an inhaler, a vaporizer, a humidifier, a mask, a mister, a fogger, and/or a sprayer, among other mechanisms, devices, and/or systems that are possible, each of which is contemplated herein. That is, various embodiments of the delivery mechanism 206D are configured to emit and/or expel the mixture 204D in the form of a spray, a fine spray, a mist, a stream, a vapor, an aerosol, a sprinkle, droplets, and/or a fog, etc., among other forms that are capable of being inhaled by a subject that are possible, each of which is contemplated herein.

In various embodiments, the delivery mechanism 206D is configured to combine and/or facilitate combining the $N_2O$ 210 stored/housed in the reservoir 208, the first additive 214A stored/housed in the reservoir 212A, the second additive 214B stored/housed in the reservoir 212B, the third additive 214C stored/housed in the reservoir 212C, and each additional additive 214n stored/housed in a respective reservoir 212n to generate and/or facilitate generating the mixture 204D. Since the mixture 204D includes a combination of the $N_2O$ 210, the first additive 214A, the second additive 214B, the third additive 214C, and one or more additional additives 214n, the delivery mechanism 206D, in some embodiments, is configured to simultaneously deliver the $N_2O$ 210, the first additive 214A, the second additive 214B, the third additive 214C, and each additional additive 214n to the mouth and/or nose of the subject and/or user for inhalation by the subject/user.

In various embodiments, the mixture 204D includes at least 20% of the $N_2O$ 210. That is, various embodiments of the mixture 204D can include an amount of the $N_2O$ 210 in the range of about 20% to about 99% inclusive, among other amounts and/or percentages that are less than about 20% $N_2O$ 210 or greater than about 99% $N_2O$ 210 that are possible, each of which is contemplated herein.

The mixture 204D, in various embodiments, includes a minimum of about 1% of the first additive 214A, the second additive 214B, the third additive 214C, and each additional additive 214n. That is, various embodiments of the mixture 204D can include an amount of the first additive 214A, the second additive 214B, the third additive 214C, and each additional additive 214n in the range of about 1% to about 80% inclusive, among other amounts and/or percentages that are less than about 1% of the first additive 214A, the second additive 214B, the third additive 214C, and each additional additive 214n or greater than about 80% of the first additive 214A, the second additive 214B, the third additive 214C, and each additional additive 214n that are possible, each of which is contemplated herein.

In some embodiments, the $N_2O$ 210, the first additive 214A, the second additive 214B, the third additive 214C, and each additional additive 214n make up the entirety or substantially the entirety of the mixture 204D. In other embodiments, the $N_2O$ 210, the first additive 214A, the second additive 214B, the third additive 214C, and each additional additive 214n make up less than 100% of the mixture 204C.

Figure 3:
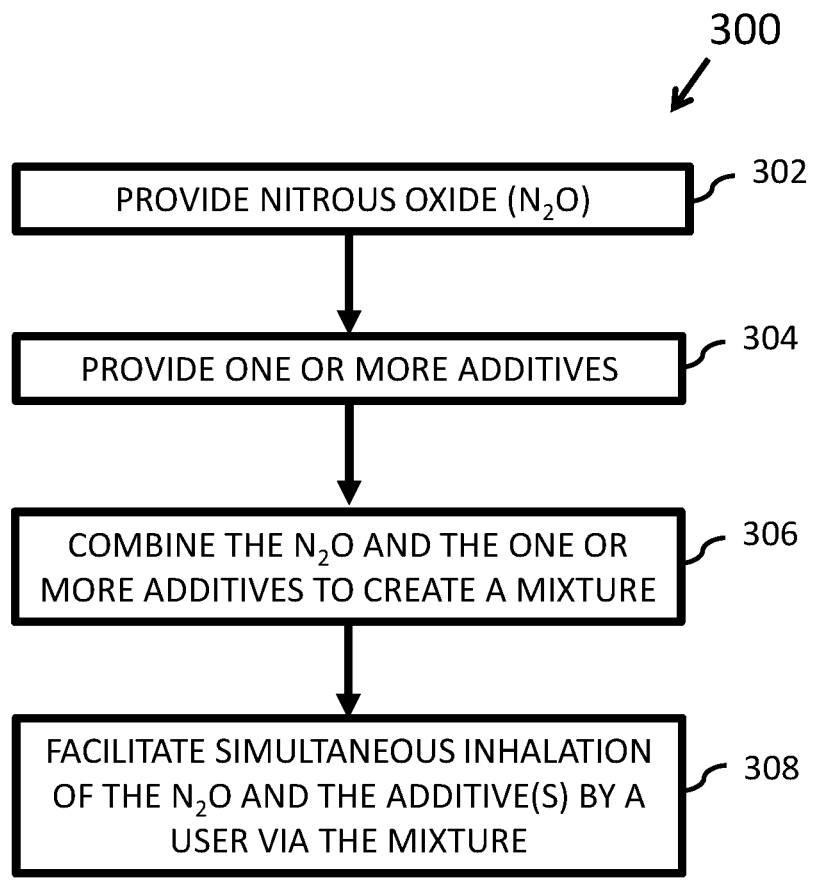
FIG. 3 is a schematic flow diagram of one embodiment of a method for providing a mixture including $N_2O$ to a subject/user.

FIG. 3 is a schematic flow diagram of one embodiment of a method 300 that can provide a mixture (e.g., mixture 104 or mixture(s) 204) including $N_2O$ to a subject/user. At least in the illustrated embodiment, the method 300 begins by providing $N_2O$ (block 302), providing one or more additives (e.g., additives 214A, 214B, 214C, and 214n, hereinafter referred to singularly or collectively simply as, additive(s) 214) (block 304), and combine the $N_2O$ and the additive(s) to form a mixture 104/204 including $N_2O$ and one or more additives (block 306).

In some embodiments, the mixture 104/204 includes at least 20% $N_2O$. In certain embodiments, the mixture 104/204 can include an amount of $N_2O$ in the range of about 20% to about 99% inclusive, among other amounts and/or percentages that are less than about 20% $N_2O$ or greater than about 99% $N_2O$ that are possible, each of which is contemplated herein.

The mixture 104/204 can include any suitable quantity of additives 214. In various embodiments, the mixture 104/204 includes one additive 214, two additives 214, three additives 214, four additives 214, or five additives 214, among other quantities that are greater than five additives 214, each of which is contemplated herein.

The mixture 104/204, in various embodiments, includes a minimum of about 1% of the additive(s) 214. That is, various embodiments of the mixture 104/204 can include an amount of the additive(s) 214 in the range of about 1% to about 80% inclusive, among other amounts and/or percentages that are less than about 1% of the additive(s) 214 or greater than about 80% of the additive(s) 214 that are possible, each of which is contemplated herein.

The method 300 further includes facilitating simultaneous inhalation of the $N_2O$ and the additive(s) by a user (block 308). In various embodiments, the simultaneous inhalation of the $N_2O$ and the additive(s) by the user is facilitated by a delivery mechanism (e.g., delivery mechanism 106, 206A, 206B, 206C, and 206D).

As discussed above, since a mixture 104/204 includes a combination of $N_2O$ and one or more additives, the delivery mechanism 106 is capable of simultaneously delivering the $N_2O$ and the one or more additives to the mouth and/or nose of a subject (e.g., a user) for inhalation by the subject/user.

Figure 4:
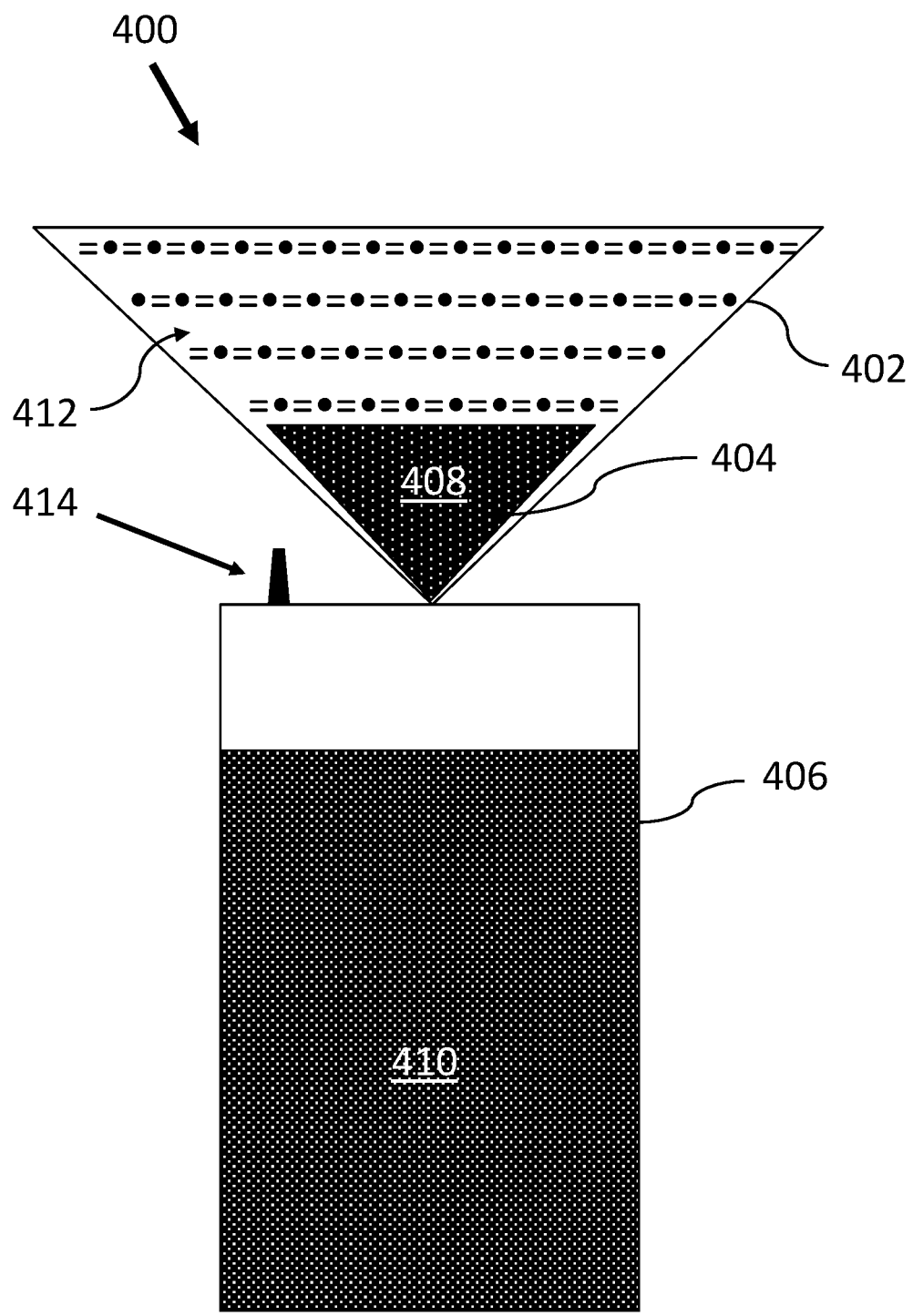
FIG. 4 is a schematic diagram of another embodiment of an apparatus that can provide a mixture including $N_2O$ to a subject/user.

FIG. 4 is a schematic diagram of another embodiment of an apparatus 400 that can provide a mixture including $N_2O$ to a subject/user. At least in the illustrated embodiment, the apparatus 400 includes a mask 402 with an integrated reservoir 404 coupled to a reservoir 406.

The mask 402 may include any suitable shape(s) that is/are capable of allowing/enabling a user to cover the user's mouth and/or nose with the mask 402. Similarly, the mask 402 may include any suitable dimension(s) that is/are capable of allowing/enabling a user to cover the user's mouth and/or nose with the mask 402.

In some embodiments, the mask 402 includes one or more shapes and/or one or more dimensions to allow/enable the user to cover the user's mouth with the mask 402. In other embodiments, the mask 402 includes one or more shapes and/or one or more dimensions to allow/enable the user to cover the user's nose with the mask 402. In further embodiments, the mask 402 includes one or more shapes and/or one or more dimensions to allow/enable the user to cover the user's mouth and nose with the mask 402.

The integrated reservoir 404 may include any suitable size and/or shape that enables/allows the integrated reservoir 404 to be integrated with the mask 402. In various embodiments, the integrated reservoir 404 is housed within and/or coupled to the exterior of the mask 402.

In various embodiments, the integrated reservoir 404 is configured to store an additive 408. In other embodiments, the integrated reservoir 404 is configured to store multiple additives 408.

The quantity of additives 408 stored in the integrated reservoir 404 may include any suitable quantity of additives 408 that is/are known or developed in the future. In some embodiments, the integrated reservoir 404 can store a single additive 408. In additional or alternative embodiments, the integrated reservoir 404 can store a plurality of additives 408 (e.g., two additives 408, three additives 408, four additives 408, five additives 408, "n" additives 408, etc.).

As discussed elsewhere herein, an additive 408 can include any suitable substance, liquid, and/or gas that can be suitably combined with a gas 410 to form a mixture 412, as discussed elsewhere herein. Example additives 408 can include, but are not limited to, air (e.g., pressurized air, compressed air, atmospheric air, etc.), $O_2$, a *cannabis* extract, an essential oil, a silver and/or silver compound, an herb and/or herbal extract, a supplement, a medication, a vitamin, a nutrient, caffeine, a nano-capacitor, $H_2O$, $H_2O_2$, and/or a flavoring, etc., among other suitable additives 408 that are possible, each of which is contemplated herein.

A *cannabis* extract can include any suitable substance that is known or developed in the future capable of being extracted from a *cannabis* plant (e.g., *Cannabis sativa*) that can be suitably combined with the gas 410 to form the mixture 412 in the mask 402. Example *cannabis* extracts can include, but are not limited to, CBD extract and/or a THC extract, etc., among other suitable extract from a *cannabis* plant that are possible, each of which is contemplated herein.

An essential oil can include any suitable essential oil and/or combination of essential oils that is/are known or developed in the future that can be suitably combined with the gas 410 to form the mixture 412 in the mask 402. Example essential oils include, but are not limited to, lemon oil, peppermint oil, lavender oil, tee tree oil, eucalyptus oil, clove oil, chamomile oil, orange oil, spearmint oil, rosemary oil, grapefruit oil, oregano oil, ginger oil, lemongrass oil, spruce oil, pine oil, sandalwood oil, cedarwood oil, marjoram oil, clary sage oil, valerian oil, patchouli oil, vetiver oil, ylang ylang oil, frankincense oil, myrrh oil, neroli oil, and/or bergamot oil, among other suitable essential oils that are possible, each of which is contemplated herein.

A silver may include any suitable silver and/or silver compound that is known or developed in the future that can be suitably combined with the gas 410 to form the mixture 412 in the mask 402. Example silvers may include, but are not limited to, a colloidal silver, nano-silver, $Ag_2O$, etc., among other suitable silvers and/or silver compounds that are possible, each of which is contemplated herein. In some embodiments, a silver can include a colloidal silver and/or nano-silver manufactured by SilverCeuticals® LLC of Lindon, Utah.

An herb and/or herbal extract may include any suitable herb and/or extract from any suitable herb that is known or developed in the future that can be suitably combined with the gas 410 to form the mixture 412 in the mask 402. Example herbs and/or extracts from a herb can include, but are not limited to, echinacea, ginseng, Siberian, ginseng, *Ginkgo biloba*, elderberry, St. John's wort, turmeric, ginger, valerian, chamomile, mint, clover, henbane, mistletoe, monkshood, pasqueflower, primrose, vervain, garlic, saw palmetto, goldenseal, aloe, tulsi, amla, ashwagandha, gotu kola, neem, cumin, peppermint, and/or cinnamon, etc., among other herbs and/or herbal extracts that are possible, each of which is contemplated herein.

A supplement may include any suitable supplement that is known or developed in the future that can be suitably combined with the gas 410 to form the mixture 412 in the mask 402. Example supplements can include, but are not limited to, fish oil, a probiotic, Omega-3, curcumin, collagen, CoQ10, chondroitin, coconut oil, rose hips, melatonin, apple cider vinegar, green tea and/or green tea extract, cocoa and/or cocoa extract, and/or dark chocolate and/or dark chocolate extract, etc., among other supplements that are possible, each of which is contemplated herein.

A medication may include any suitable medication that is known or developed in the future that can be suitably combined with the gas 410 to form the mixture 412 in the mask 402. In various embodiments, a medication includes any medication that can be effectively absorbed through the lungs, without notably toxicity, and that can include a beneficial (perceived and/or substantiated) effect on the body of a subject (e.g., human, animal, etc.). Example medications can include, but are not limited to, a medication for asthma, COPD, an infection, inflammation, cystic fibrosis, and/or an autoimmune disease, etc., among other medications that are possible, each of which is contemplated herein.

A vitamin may include any suitable vitamin or multivitamin that is known or developed in the future that can be suitably combined with the gas 410 to form the mixture 412 in the mask 402. Example vitamins include, but are not limited to, Vitamin A, Vitamin B (e.g., Vitamin B1 (Thiamine), Vitamin B2 (Riboflavin), Vitamin B3 (Niacin), Vitamin B5 (Pantothenic Acid), Vitamin B6 (Pyridoxine), Vitamin B7 (Biotin), Vitamin B9 (Folate or Folic Acid), Vitamin B12 (Cobalamin), a B-complex, etc.), Vitamin C (Ascorbic Acid), Vitamin D, Vitamin E, Vitamin K, and/or Choline, etc., among other vitamins and/or multivitamins that are possible, each of which is contemplated herein.

A nutrient may include any suitable nutrient and/or mineral that is known or developed in the future that can be suitably combined with the gas 410 to form the mixture 412 in the mask 402. Example nutrients include, but are not limited to, Calcium, Chloride, Chromium, Copper, Fluoride, Iodine, Iron, Magnesium, Manganese, Molybdenum, Phosphorus, Potassium, Selenium, Sodium, and/or Zinc, etc., among other nutrients and/or minerals that are possible, each of which is contemplated herein.

A flavoring may include any suitable flavoring that is known or developed in the future that can be suitably combined with the gas to form the mixture 412 in the mask. Example flavorings include, but are not limited to, a fruit flavoring (e.g., apple, strawberry, raspberry, pear, blackberry, blueberry, peach, plum, apricot, banana, pineapple, watermelon, grape, cherry, mango, papaya, kiwi, cantaloupe, orange, clementine, lemon, grapefruit, and/or lime, etc.), a mint flavoring (e.g., spearmint, peppermint, etc.), a chocolate flavoring, a coffee flavoring, and/or a vanilla flavoring, etc., among other flavorings that are possible, each of which is contemplated herein.

A nano-capacitor may include any suitable nano-capacitor and/or type of nano-capacitor that is known or developed in the future. In some embodiments, the nano-capacitor includes a nano-capacitor manufactured by nCAP® Technologies LLC of Heber City, Utah.

The reservoir 406 may include any suitable size and/or shape that enables/allows the reservoir 406 to be coupled (e.g., permanently coupled) and/or connected to the mask 402. In certain embodiments, the reservoir 406 is coupled to the exterior of the mask 402.

In various embodiments, the reservoir 406 is configured to store a gas 410. In other embodiments, the reservoir 406 is configured to store multiple gases 410.

The gas 410, in various embodiments, includes $N_2O$ gas. In some embodiments, the gas 410 is pure $N_2O$ (e.g., 100% $N_2O$ gas).

In other embodiments, the gas 410 includes $N_2O$ combined one or more other gases. In some embodiments, the gas 410 includes an amount of $N_2O$ in the range of about 0.1% to about 99.9% $N_2O$ by weight and/or volume. In addition, the gas 410 can further include a corresponding amount of the other gas or gases in the range of about 0.1% to about 99.9% $N_2O$ by weight and/or volume such that the gas 410 is comprised of $N_2O$ and the other gas or gasses.

The other gas or gases that may be combined with the $N_2O$ can include any suitable gas or gases that is/are known, developed, or discovered in the future. Example gases can include, but are not limited to, pressurized air, compressed air, atmospheric air, and/or pure oxygen ($O_2$), etc., among other gases that are possible, each of which is contemplated herein.

In various embodiments, the apparatus 400 includes an actuator 414. The actuator 414 may include any suitable actuating mechanism/device and/or type of actuator 414 that is known or developed in the future. Example actuators 414 include, but are not limited to, a trigger, a pump, a sprayer, an atomizer, and/or a mister, etc., among other devices and/or type(s) of actuating devices that are possible, each of which is contemplated herein.

In various embodiments, the actuator is in fluid and/or gaseous communication with the integrated reservoir 404 and the reservoir 406. The actuator 414, in various embodiments, is configured to simultaneously or substantially simultaneously release at least a portion of the additive(s) 408 stored in the integrated reservoir 404 and at least a portion of the gas 410 stored in the reservoir 406 into the mask 402 upon actuation. Upon release, the mask 402 is configured to create and/or facilitate creating the mixture 412 by enabling and/or allowing the additive(s) 408 and the gas 410 to mix and/or combine in the mask 402.

The mixture 412 created in the mask 402 may include any suitable amount of $N_2O$. That is, the integrated reservoir 404 and/or the additive(s) 408, the reservoir and/or the gas 410, and the trigger 414 may be calibrated in a manner that results in the mixture 412 including a predetermined amount and/or percentage of $N_2O$, by weight and/or volume.

In various embodiments, the mixture 412 includes a predetermined amount and/or percentage of $N_2O$ in the range of about 10% to about 99%, by weight and/or volume. In some embodiments, the mixture 412 includes a predetermined amount and/or percentage of $N_2O$ in the range of about 20% to about 50%, by weight and/or volume. In certain embodiments, the mixture 412 includes a predetermined amount and/or percentage of $N_2O$ of about 35%, by weight and/or volume.

The mixture 412 may include any suitable dosage and/or amount of the additive(s) 408 and/or suitable dosage and/or amount of the gas 410. In some embodiments, the amount of the additive(s) 408 stored in the integrated reservoir 404 and the amount of the gas 410 stored in the reservoir 406 are amounts to create one dosage of the mixture 412 in the mask 402 such that the apparatus 400 can define a single use device. In other embodiments, the amount of the additive(s) 408 stored in the integrated reservoir 404 and the amount of the gas 410 stored in the reservoir 406 are amounts to create multiples dosage of the mixture 412 in the mask 402 such that the apparatus 400 can define a multi-use device, which can be any suitable quantity of dosages. In certain embodiments, the quantity of dosages corresponds to a particular treatment and/or regimen for the user, as prescribed by a healthcare professional.

In some embodiments, the mixture includes 50% $N_2O$, by weight and/or volume, and 50% $O_2$, by weight and/or volume, among other amount(s) and/or percentage(s) that is/are possible, each of which is contemplated herein. In other embodiments, the mixture includes 45% $N_2O$, by weight and/or volume, and 55% $O_2$, by weight and/or volume, among other amount(s) and/or percentage(s) that is/are possible, each of which is contemplated herein. In other embodiments, the mixture includes 40% $N_2O$, by weight and/or volume, and 60% $O_2$, by weight and/or volume, among other amount(s) and/or percentage(s) that is/are possible, each of which is contemplated herein.

Figure 5:
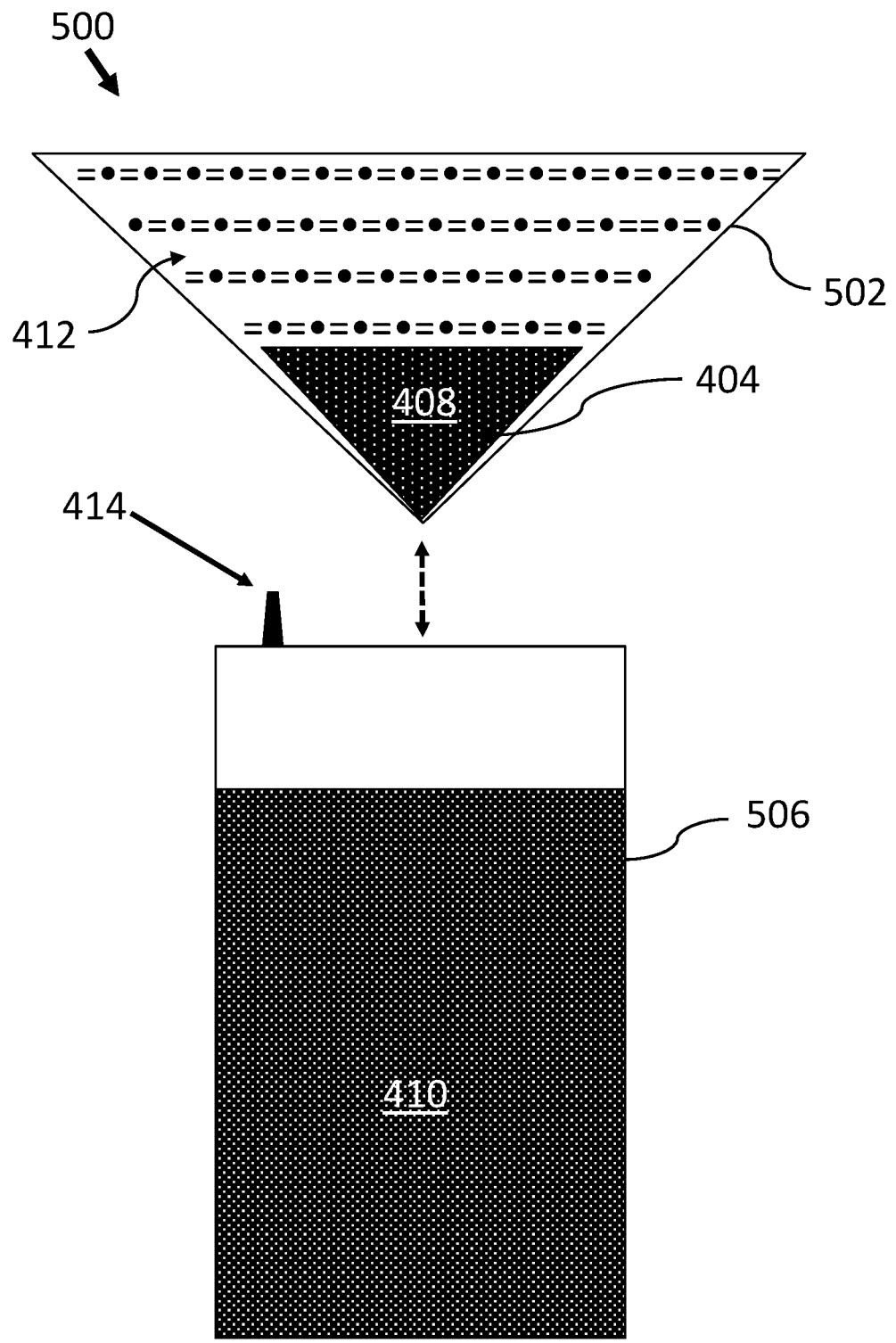
FIG. 5 is a schematic diagram of still another embodiment of an apparatus that can provide a mixture including $N_2O$ to a subject/user.

FIG. 5 is a schematic diagram of yet another embodiment of an apparatus 500 that can provide a mixture including $N_2O$ to a subject/user. At least in the illustrated embodiment, the apparatus 500 includes an integrated reservoir 404 configured to store one or more additives 408 and an actuator 414 similar to the apparatus 400 discussed elsewhere herein. The apparatus 500, in various embodiments, further includes a mask 502 that is configured to create and/or facilitate creating the mixture 412 similar to the mixture 412 created in the mask 402 and a reservoir 506 configured to store a gas 410 similar to the gas 410 discussed with reference to apparatus 400.

The mask 502 may include any suitable shape(s) that is/are capable of allowing/enabling a user to cover the user's mouth and/or nose with the mask 502. Similarly, the mask 502 may include any suitable dimension(s) that is/are capable of allowing/enabling a user to cover the user's mouth and/or nose with the mask 502.

In some embodiments, the mask 502 includes one or more shapes and/or one or more dimensions to allow/enable the user to cover the user's mouth with the mask 502. In other embodiments, the mask 502 includes one or more shapes and/or one or more dimensions to allow/enable the user to cover the user's nose with the mask 502. In further embodiments, the mask 502 includes one or more shapes and/or one or more dimensions to allow/enable the user to cover the user's mouth and nose with the mask 502.

The integrated reservoir 404 may include any suitable size and/or shape that enables/allows the integrated reservoir 404 to be integrated with the mask 502. In various embodiments, the integrated reservoir 404 is housed within and/or coupled to the exterior of the mask 502.

In various embodiments, the integrated reservoir 404 is configured to store an additive 408 similar to the embodiments discussed elsewhere herein. In other embodiments, the integrated reservoir 404 is configured to store multiple additives 408, similar to the embodiments discussed elsewhere herein.

The actuator 414 of the apparatus 500, in various embodiments, is configured to release at least a portion of the additive(s) 408 stored in the integrated reservoir 404 and at least a portion of the gas 410 stored in the reservoir 506 into the mask 502 upon actuation. Upon release, the mask 502 is configured to create and/or facilitate creating the mixture 412 by enabling and/or allowing the additive(s) 408 and the gas 410 to mix and/or combine in the mask 502.

The mixture 412 created in the mask 502 may include any suitable amount of $N_2O$. That is, the integrated reservoir 404 and/or the additive(s) 408, the reservoir 506 and/or the gas 410, and the trigger 414 may be calibrated in a manner that results in the mixture 412 including a predetermined amount and/or percentage of $N_2O$, by weight and/or volume, in the mask 502.

In various embodiments, the mixture 412 includes a predetermined amount and/or percentage of $N_2O$ in the range of about 10% to about 99%, by weight and/or volume. In some embodiments, the mixture 412 includes a predetermined amount and/or percentage of $N_2O$ in the range of about 20% to about 50%, by weight and/or volume. In certain embodiments, the mixture 412 includes a predetermined amount and/or percentage of $N_2O$ of about 35%, by weight and/or volume.

In some embodiments, the mixture includes 50% $N_2O$, by weight and/or volume, and 50% $O_2$, by weight and/or volume, among other amount(s) and/or percentage(s) that is/are possible, each of which is contemplated herein. In other embodiments, the mixture includes 45% $N_2O$, by weight and/or volume, and 55% $O_2$, by weight and/or volume, among other amount(s) and/or percentage(s) that is/are possible, each of which is contemplated herein. In other embodiments, the mixture includes 40% $N_2O$, by weight and/or volume, and 60% $O_2$, by weight and/or volume, among other amount(s) and/or percentage(s) that is/are possible, each of which is contemplated herein.

The mixture 412 may include any suitable dosage and/or amount of the additive(s) 408 and/or suitable dosage and/or amount of the gas 410. In some embodiments, the amount of the additive(s) 408 stored in the integrated reservoir 404 and the amount of the gas 410 stored in the reservoir 506 are amounts to create one dosage of the mixture 412 in the mask 502 such that the apparatus 500 can define a single use device. In other embodiments, the amount of the additive(s) 408 stored in the integrated reservoir 404 and the amount of the gas 410 stored in the reservoir 506 are amounts to create multiples dosage of the mixture 412 in the mask 502 such that the apparatus 500 can define a multi-use device, which can be any suitable quantity of dosages. In certain embodiments, the quantity of dosages corresponds to a particular treatment and/or regimen for the user, as prescribed by a healthcare professional.

In various embodiments, the mask 502 is capable of being attached and detached from the reservoir 506 one or more times. As such, the mask 502 and the reservoir 506 can be considered detachably coupleable to one another. That is, the mask 502 and the reservoir 506 are individually configured to be able to couple and decouple from one another.

Being detachably coupleable to one another, various embodiments of the mask 502 and/or the reservoir 506 may be replaceable, refillable, and/or exchangeable. That is, a new mask 502 including a new integrated reservoir 404 may replace a previous mask 502 including a previous integrated reservoir 404 on the reservoir 506 of the apparatus 500. Similarly, a new reservoir 506 may replace a previous reservoir 506 on the mask 502 of the apparatus 500.

The integrated reservoir 404 and the reservoir 506 may store amounts of the additive(s) 408 and the gas 410 so that equal dosage amounts of the additive(s) 408 and the gas 410 are used to create the mixture 412. In some embodiments, the integrated reservoir 404 and the reservoir 506 store different dosage amounts of the additive(s) 408 and the gas 410. Here, the different dosage amounts of the additive(s)

408 and the gas 410 can account for spoilage/expiration of one or more additives 408 and/or the gas 410. Thus, by replacing the mask 502 and/or the reservoir 506, new, unexpired, and/or unspoiled additive(s) 408 and/or gas 410 can be safely and/or effectively used, respectively. Further, a new mask 502 can provide a more hygienic environment for a user and/or enable multiple users to use the apparatus 500.

Figure 6:
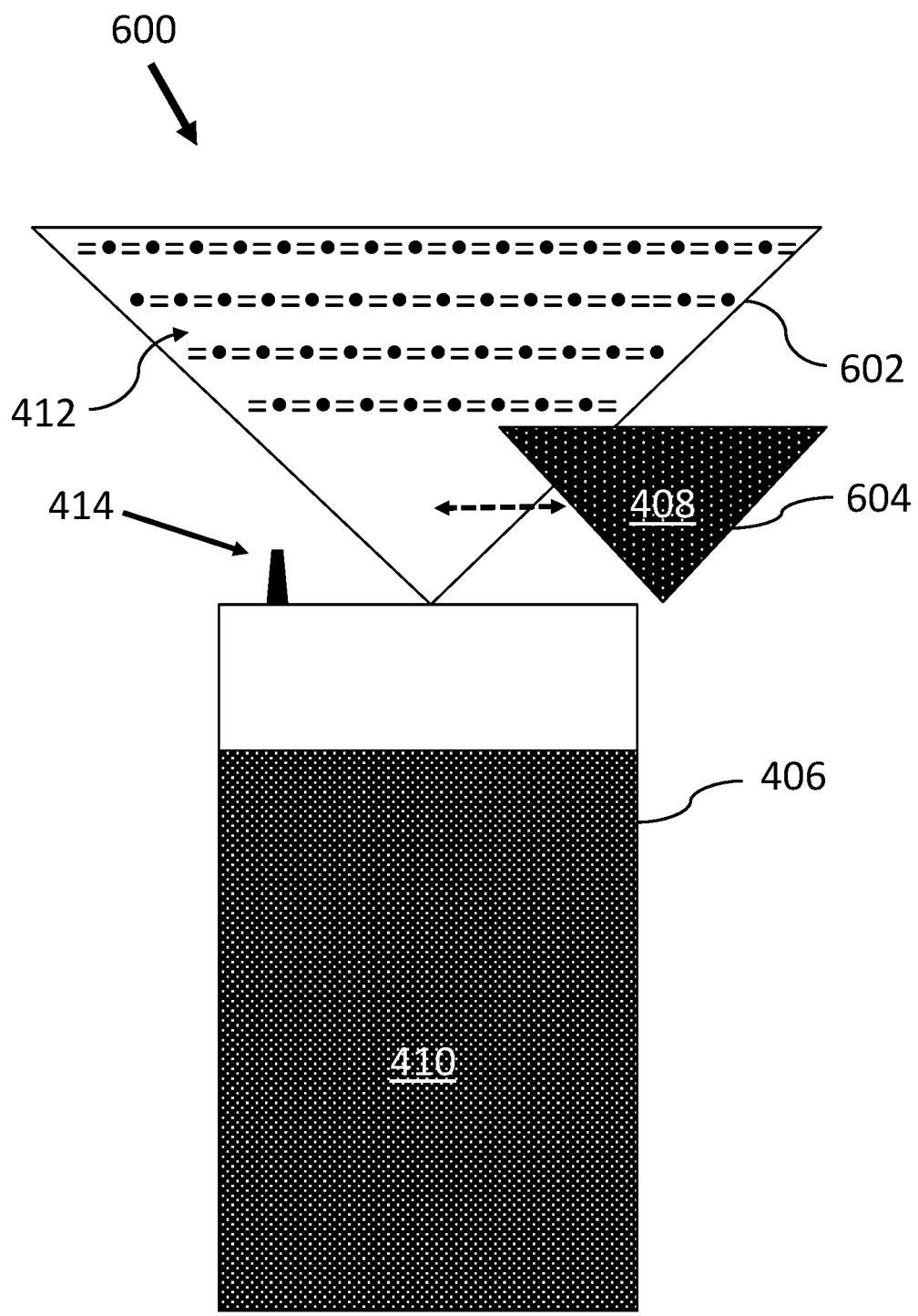
FIG. 6 is a schematic diagram of yet another embodiment of an apparatus that can provide a mixture including $N_2O$ to a subject/user.

FIG. 6 is a schematic diagram of still another embodiment of an apparatus 600 that can provide a mixture including $N_2O$ to a subject/user. At least in the illustrated embodiment, the apparatus 600 includes a reservoir 606 configured to store a gas 410 and an actuator 414 similar to the apparatus 400 discussed elsewhere herein. The apparatus 600, in various embodiments, further includes a mask 602 that is configured to create and/or facilitate creating the mixture 412 similar to the mixture 412 created in the mask 402 and a reservoir 604 configured to store one or more additives 408 similar to the additive(s) 408 discussed with reference to apparatus 400.

The mask 602 may include any suitable shape(s) that is/are capable of allowing/enabling a user to cover the user's mouth and/or nose with the mask 602. Similarly, the mask 602 may include any suitable dimension(s) that is/are capable of allowing/enabling a user to cover the user's mouth and/or nose with the mask 602.

In some embodiments, the mask 602 includes one or more shapes and/or one or more dimensions to allow/enable the user to cover the user's mouth with the mask 602. In other embodiments, the mask 602 includes one or more shapes and/or one or more dimensions to allow/enable the user to cover the user's nose with the mask 602. In further embodiments, the mask 602 includes one or more shapes and/or one or more dimensions to allow/enable the user to cover the user's mouth and nose with the mask 602.

In various embodiments, the mask 602 is capable of being attached and detached from the reservoir 604 one or more times. As such, the mask 602 and the reservoir 604 can be considered detachably coupleable to one another. That is, the mask 602 and the reservoir 604 are individually configured to be able to couple and decouple from one another.

Being detachably coupleable to one another, various embodiments of the mask 602 and/or the reservoir 604 may be replaceable, refillable, and/or exchangeable. That is, a new mask 602 may replace a previous mask 602 and/or a new reservoir 604 may replace a previous reservoir 604 of the apparatus 600.

The reservoir 604 and the reservoir 406 may store amounts of the additive(s) 408 and the gas 410 so that equal dosage amounts of the additive(s) 408 and the gas 410 are used to create the mixture 412. In some embodiments, the reservoir 604 and the reservoir 406 store different dosage amounts of the additive(s) 408 and the gas 410. Here, the different dosage amounts of the additive(s) 408 and the gas 410 can account for spoilage/expiration of one or more additives 408. Thus, by replacing the reservoir 604, new, unexpired, and/or unspoiled additive(s) 408 can be safely and/or effectively used. Further, a new mask 602 can provide a more hygienic environment for a user and/or enable multiple users to use the apparatus 600.

The reservoir 604 may include any suitable size and/or shape that enables/allows the reservoir 604 to be detachably coupled to the mask 602. In various embodiments, the reservoir 604 is detachably coupled to an interior of the mask 602 and/or detachably coupleable to the exterior of the mask 602.

In various embodiments, the reservoir 604 is configured to store an additive 408 similar to the embodiments discussed elsewhere herein. In other embodiments, the reservoir 604 is configured to store multiple additives 408, similar to the embodiments discussed elsewhere herein.

The actuator 414 of the apparatus 600, in various embodiments, is configured to release at least a portion of the additive(s) 408 stored in the reservoir 604 and at least a portion of the gas 410 stored in the reservoir 406 into the mask 602 upon actuation. Upon release, the mask 602 is configured to create and/or facilitate creating the mixture 412 by enabling and/or allowing the additive(s) 408 and the gas 410 to mix and/or combine in the mask 602.

The mixture 412 created in the mask 602 may include any suitable amount of $N_2O$. That is, the reservoir 604 and/or the additive(s) 408, the reservoir 406 and/or the gas 410, and the trigger 414 may be calibrated in a manner that results in the mixture 412 including a predetermined amount and/or percentage of $N_2O$, by weight and/or volume, in the mask 602.

In various embodiments, the mixture 412 includes a predetermined amount and/or percentage of $N_2O$ in the range of about 10% to about 99%, by weight and/or volume. In some embodiments, the mixture 412 includes a predetermined amount and/or percentage of $N_2O$ in the range of about 20% to about 50%, by weight and/or volume. In certain embodiments, the mixture 412 includes a predetermined amount and/or percentage of $N_2O$ of about 35%, by weight and/or volume.

In some embodiments, the mixture includes 50% $N_2O$, by weight and/or volume, and 50% $O_2$, by weight and/or volume, among other amount(s) and/or percentage(s) that is/are possible, each of which is contemplated herein. In other embodiments, the mixture includes 45% $N_2O$, by weight and/or volume, and 55% $O_2$, by weight and/or volume, among other amount(s) and/or percentage(s) that is/are possible, each of which is contemplated herein. In other embodiments, the mixture includes 40% $N_2O$, by weight and/or volume, and 60% $O_2$, by weight and/or volume, among other amount(s) and/or percentage(s) that is/are possible, each of which is contemplated herein.

The mixture 412 may include any suitable dosage and/or amount of the additive(s) 408 and/or suitable dosage and/or amount of the gas 410. In some embodiments, the amount of the additive(s) 408 stored in the reservoir 604 and the amount of the gas 410 stored in the reservoir 406 are amounts to create one dosage of the mixture 412 in the mask 602 such that the apparatus 600 can define a single use device. In other embodiments, the amount of the additive(s) 408 stored in the reservoir 604 and the amount of the gas 410 stored in the reservoir 406 are amounts to create multiples dosage of the mixture 412 in the mask 602 such that the apparatus 600 can define a multi-use device, which can be any suitable quantity of dosages. In certain embodiments, the quantity of dosages corresponds to a particular treatment and/or regimen for the user, as prescribed by a healthcare professional.

Figure 7:
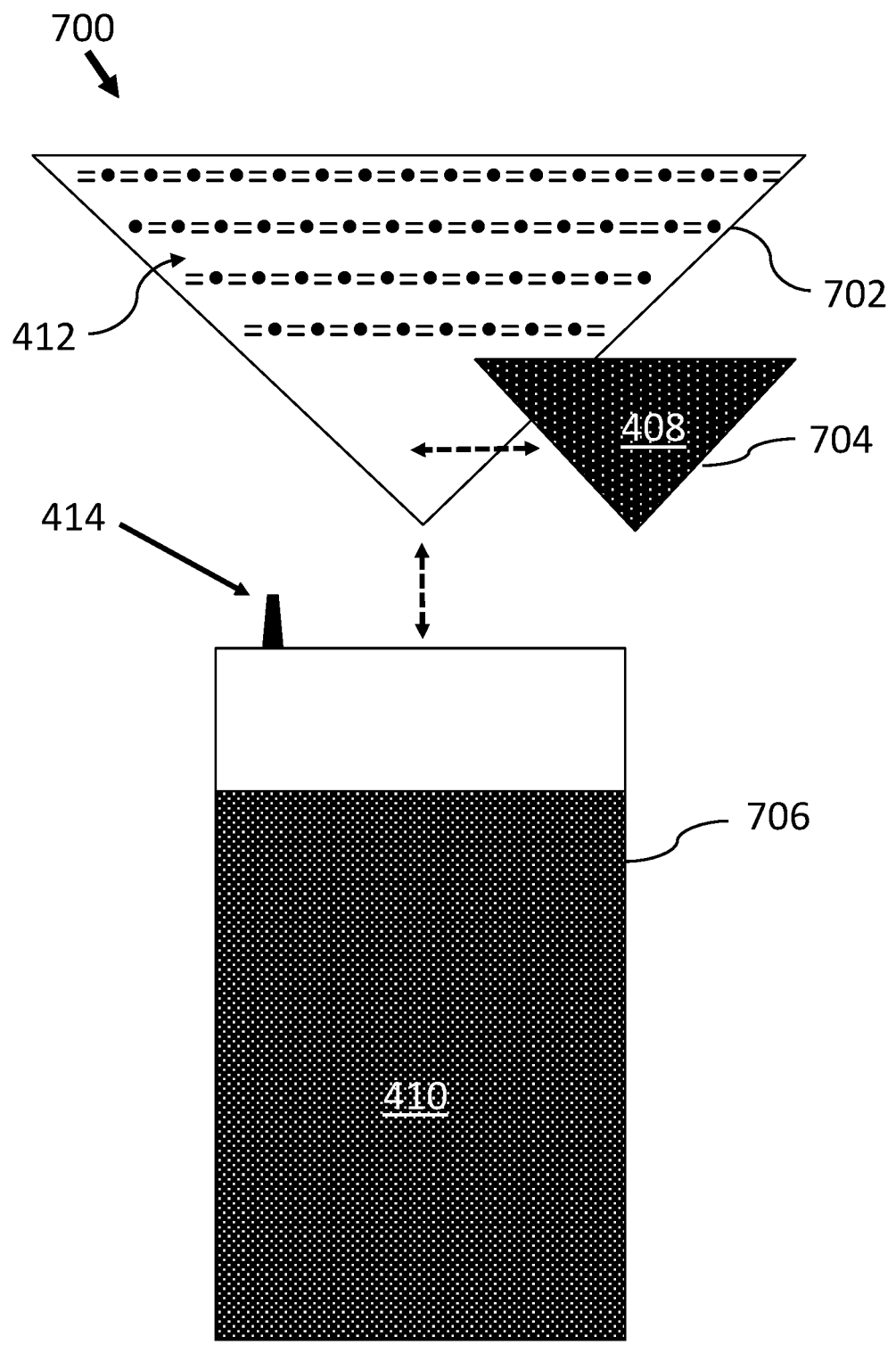
FIG. 7 is a schematic diagram of a further embodiment of an apparatus that can provide a mixture including $N_2O$ to a subject/user.

FIG. 7 is a schematic diagram of a further embodiment of an apparatus 700 that can provide a mixture including $N_2O$ to a subject/user. At least in the illustrated embodiment, the apparatus 700 includes a mask 702 that is configured to create and/or facilitate creating the mixture 412 similar to the mixture 412 created in the mask 402, a reservoir 704 configured to store one or more additives 408 similar to the additive(s) 408 discussed elsewhere herein, a reservoir 706 configured to store a gas 410 similar to the gas 410 discussed elsewhere herein, and an actuator 414 similar to the various embodiments of an actuator 414 discussed elsewhere herein.

The mask 702 may include any suitable shape(s) that is/are capable of allowing/enabling a user to cover the user's mouth and/or nose with the mask 702. Similarly, the mask 702 may include any suitable dimension(s) that is/are capable of allowing/enabling a user to cover the user's mouth and/or nose with the mask 702.

In some embodiments, the mask 702 includes one or more shapes and/or one or more dimensions to allow/enable the user to cover the user's mouth with the mask 702. In other embodiments, the mask 702 includes one or more shapes and/or one or more dimensions to allow/enable the user to cover the user's nose with the mask 702. In further embodiments, the mask 702 includes one or more shapes and/or one or more dimensions to allow/enable the user to cover the user's mouth and nose with the mask 702.

In various embodiments, the mask 702 is capable of being attached and detached from the reservoir 704 one or more times. As such, the mask 702 and the reservoir 704 can be considered detachably coupleable to one another. That is, the mask 702 and the reservoir 704 are individually configured to be able to couple and decouple from one another.

Being detachably coupleable to one another, various embodiments of the mask 702 and/or the reservoir 704 may be replaceable, refillable, and/or exchangeable. That is, a new mask 702 may replace a previous mask 702 and/or a new reservoir 704 may replace a previous reservoir 704 of the apparatus 700.

The reservoir 704 may include any suitable size and/or shape that enables/allows the reservoir 704 to be detachably coupled to the mask 702. In various embodiments, the reservoir 704 is detachably coupled to an interior of the mask 702 and/or detachably coupleable to the exterior of the mask 702.

In various embodiments, the reservoir 704 is configured to store an additive 408 similar to the embodiments discussed elsewhere herein. In other embodiments, the reservoir 704 is configured to store multiple additives 408, similar to the embodiments discussed elsewhere herein.

In various embodiments, the mask 702 is further capable of being attached and detached from the reservoir 706 one or more times. As such, the mask 702 and the reservoir 706 can be considered detachably coupleable to one another. That is, the mask 702 and the reservoir 706 are individually configured to be able to couple and decouple from one another.

Being detachably coupleable to one another, various embodiments of the mask 702 and/or the reservoir 706 may be replaceable, refillable, and/or exchangeable. That is, a new mask 702 may replace a previous mask 702. Similarly, a new reservoir 706 may replace a previous reservoir 706.

The reservoir 704 and the reservoir 706 may store amounts of the additive(s) 408 and the gas 410 so that equal dosage amounts of the additive(s) 408 and the gas 410 are used to create the mixture 412. In some embodiments, the reservoir 704 and the reservoir 706 store different dosage amounts of the additive(s) 408 and the gas 410. Here, the different dosage amounts of the additive(s) 408 and the gas 410 can account for spoilage/expiration of one or more additives 408. Thus, by replacing the reservoir 704, new, unexpired, and/or unspoiled additive(s) 408 can be safely and/or effectively used. Further, a new mask 702 can provide a more hygienic environment for a user and/or enable multiple users to use the apparatus 700.

The actuator 414 of the apparatus 700, in various embodiments, is configured to release at least a portion of the additive(s) 408 stored in the reservoir 704 and at least a portion of the gas 410 stored in the reservoir 706 into the mask 702 upon actuation. Upon release, the mask 702 is configured to create and/or facilitate creating the mixture 412 by enabling and/or allowing the additive(s) 408 and the gas 410 to mix and/or combine in the mask 702.

The mixture 412 created in the mask 702 may include any suitable amount of $N_2O$. That is, the reservoir 704 and/or the additive(s) 408, the reservoir 706 and/or the gas 410, and the trigger 414 may be calibrated in a manner that results in the mixture 412 including a predetermined amount and/or percentage of $N_2O$, by weight and/or volume, in the mask 702.

In various embodiments, the mixture 412 includes a predetermined amount and/or percentage of $N_2O$ in the range of about 10% to about 99%, by weight and/or volume. In some embodiments, the mixture 412 includes a predetermined amount and/or percentage of $N_2O$ in the range of about 20% to about 50%, by weight and/or volume. In certain embodiments, the mixture 412 includes a predetermined amount and/or percentage of $N_2O$ of about 35%, by weight and/or volume.

In some embodiments, the mixture includes 50% $N_2O$, by weight and/or volume, and 50% $O_2$, by weight and/or volume, among other amount(s) and/or percentage(s) that is/are possible, each of which is contemplated herein. In other embodiments, the mixture includes 45% $N_2O$, by weight and/or volume, and 55% $O_2$, by weight and/or volume, among other amount(s) and/or percentage(s) that is/are possible, each of which is contemplated herein. In other embodiments, the mixture includes 40% $N_2O$, by weight and/or volume, and 60% $O_2$, by weight and/or volume, among other amount(s) and/or percentage(s) that is/are possible, each of which is contemplated herein.

The mixture 412 may include any suitable dosage and/or amount of the additive(s) 408 and/or suitable dosage and/or amount of the gas 410. In some embodiments, the amount of the additive(s) 408 stored in the reservoir 704 and the amount of the gas 410 stored in the reservoir 706 are amounts to create one dosage of the mixture 412 in the mask 702 such that the apparatus 700 can define a single use device. In other embodiments, the amount of the additive(s) 408 stored in the reservoir 704 and the amount of the gas 410 stored in the reservoir 706 are amounts to create multiples dosage of the mixture 412 in the mask 702 such that the apparatus 700 can define a multi-use device, which can be any suitable quantity of dosages. In certain embodiments, the quantity of dosages corresponds to a particular treatment and/or regimen for the user, as prescribed by a healthcare professional.

Various embodiments of the apparatus 400, 500, 600, and/or 700 may include an inhaler, an atomizer, a vaporizer, a humidifier, a mister, a fogger, and/or a sprayer, etc., among other apparatus, devices, and/or systems that are possible, each of which is contemplated herein. Further, some embodiments of the apparatus 400, 500, 600, and/or 700 may include and/or define personal devices/apparatus and/or portable devices/apparatus.

Figure 8:
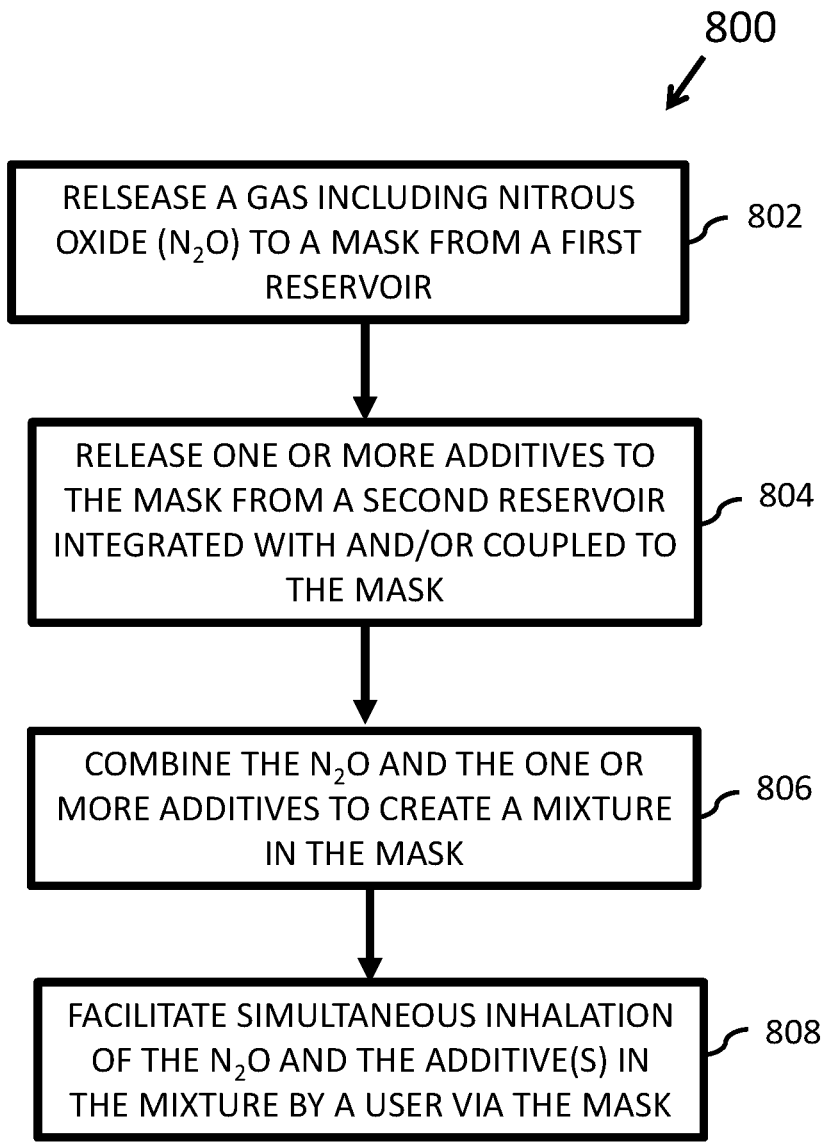
FIG. 8 is a schematic flow diagram of another embodiment of a method for providing a mixture including $N_2O$ to a subject/user.

FIG. 8 is a schematic flow diagram of another embodiment of a method 800 that can provide a mixture (e.g., mixture 412) including $N_2O$ to a subject/user. At least in the illustrated embodiment, the method 800 begins by releasing a gas (e.g., gas 410) including $N_2O$ to a mask (e.g., mask 402, 502, 602, 702) from a first reservoir (e.g., reservoir 406, 506, 706) that is in fluid and/or gaseous communication with the mask 402, 502, 602, 702 (block 802). The gas 410 can include any of the embodiments of a gas 410 including $N_2O$ or a combination of $N_2O$ and one or more other elements/compounds in gaseous form, as discussed elsewhere herein.

The method 800 further includes releasing one or more additives (e.g., additive(s) 408) to the mask 402, 502, 602, 702 from a second reservoir (e.g., integrated reservoir 404, reservoir 604, and reservoir 704) that is in fluid and/or gaseous communication with the mask 402, 502, 602, 702 (block 804). The additive(s) 408 can include any of the embodiments of one or more other additives 408, as discussed elsewhere herein.

The gas 410 and the additive(s) 408 can be released via actuation of an actuator (e.g., actuator 412). The actuator 412 can simultaneously or substantially simultaneously release the gas and the additive(s) 408 to the mask 402, 502, 602, 702.

The mask 402, 502, 602, 702 combines the gas 410 and the additive(s) 408 to form a mixture (e.g., mixture 412) that includes at least $N_2O$ and one or more additives 408 (block 806). The mixture 412 can include any of the embodiments of a mixture discussed elsewhere herein.

In some embodiments, the mixture includes 50% $N_2O$, by weight and/or volume, and 50% $O_2$, by weight and/or volume, among other amount(s) and/or percentage(s) that is/are possible, each of which is contemplated herein. In other embodiments, the mixture includes 45% $N_2O$, by weight and/or volume, and 55% $O_2$, by weight and/or volume, among other amount(s) and/or percentage(s) that is/are possible, each of which is contemplated herein. In other embodiments, the mixture includes 40% $N_2O$, by weight and/or volume, and 60% $O_2$, by weight and/or volume, among other amount(s) and/or percentage(s) that is/are possible, each of which is contemplated herein.

The method 800 further includes facilitating simultaneous inhalation of the $N_2O$ (e.g., via gas 410) and the additive(s) 408 by a user (block 3808). In various embodiments, the simultaneous inhalation of the $N_2O$ (e.g., via the gas 410) and the additive(s) 408 by the user is via inhaling the mixture 412 created in the mask 402, 502, 602, 702.

Reference throughout this specification to one embodiment, an embodiment, or similar language means that a particular feature, structure, or characteristic described in connection with the embodiment is included in at least one embodiment. Thus, appearances of the phrases in one embodiment, in an embodiment, and similar language throughout this specification may, but do not necessarily, all refer to the same embodiment, but mean one or more but not all embodiments unless expressly specified otherwise. The terms including, comprising, having, and variations thereof mean including but not limited to, unless expressly specified otherwise. An enumerated listing of items does not imply that any or all of the items are mutually exclusive, unless expressly specified otherwise. The terms, "a," "an," and "the," also refer to one or more unless expressly specified otherwise.

In addition, as used herein, the term, "set," can mean one or more, unless expressly specified otherwise. The term, "sets," can mean multiples of or a plurality of one or mores, ones or more, and/or ones or mores consistent with set theory, unless expressly specified otherwise.

Furthermore, the described features, structures, or characteristics of the embodiments may be combined in any suitable manner. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

It should also be noted that, in some alternative implementations, the functions noted in the block may occur out of the order noted in the Figures. For example, two blocks shown in succession may, in fact, be performed substantially concurrently, or the blocks may sometimes be performed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment.

The description of elements in each figure may refer to elements of proceeding figures. Like numbers refer to like elements in all figures, including alternate embodiments of like elements.

The various disclosed embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus, comprising:
a first reservoir configured to store a first gas, the first gas including at least nitrous oxide ($N_2O$);
a mask directly coupled to the first reservoir, the mask comprising a second reservoir integrated with the mask; and
an actuator in communication with the first reservoir and the second reservoir,
wherein:
the second reservoir is configured to store a first additive,
the actuator is configured to release at least a portion of the first additive stored in the second reservoir into the mask and release at least a portion of the first gas stored in the first reservoir into the mask upon actuation, and
the mask is configured to:
combine the first gas and the first additive to create a mixture including at least the $N_2O$ and the first additive in the mask, and
introduce the mixture to one of a mouth of a subject, a nose of the subject, or both the mouth and the nose of the subject for inhalation by the subject.

2. The apparatus of claim 1, wherein the first additive comprises one of a liquid, a second gas, a compressed gas, or a combination thereof.

3. The apparatus of claim 1, wherein the first gas comprises a first predetermined percentage of the $N_2O$ in the range of 0.1% to 100% by volume.

4. The apparatus of claim 3, wherein the first gas further comprises a second predetermined percentage of a second additive in the range of 0.1% to 99.9% by volume.

5. The apparatus of claim 1, wherein the mixture comprises a predetermined percentage of the $N_2O$ in the range of 20% to 99% by volume.

6. The apparatus of claim 1, wherein the first gas further comprises one of compressed air, pure oxygen ($O_2$), air, or atmospheric air.

7. The apparatus of claim 6, wherein:
the first additive comprises one of water ($H_2O$), hydrogen peroxide ($H_2O_2$), a *cannabis* extract, an essential oil, an herbal extract, a supplement, a medication, a vitamin, caffeine, a silver, a flavoring, a nano-capacitor, or a nutrient;
the second reservoir is further configured to store a second additive;
the second additive comprises one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient; and
the second additive is different from the first additive.

8. The apparatus of claim 1, wherein the first additive comprises one of water ($H_2O$), hydrogen peroxide ($H_2O_2$), a *cannabis* extract, an essential oil, an herbal extract, a supplement, a medication, a vitamin, caffeine, a silver, a flavoring, a nano-capacitor, or a nutrient.

9. The apparatus of claim 8, wherein:
the second reservoir is further configured to store a second additive;
the second additive comprises one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient; and
the second additive is different from the first additive.

10. An apparatus, comprising:
a mask;
a first reservoir, the first reservoir storing a first gas including at least nitrous oxide ($N_2O$);
a second reservoir, the second reservoir storing at least a first additive to the first gas; and
an actuator in communication with the first reservoir and the second reservoir,
wherein:
the first reservoir and the second reservoir are separate reservoirs,
the actuator is configured to release at least a portion of the first additive to the first gas stored in the second reservoir into the mask and release at least a portion of the first gas stored in the first reservoir into the mask upon actuation,
both the first reservoir and the second reservoir are directly coupleable to the mask, and
the mask is configured to:
combine the first gas and the first additive to create a mixture including at least the $N_2O$ and the first additive in the mask, and
introduce the mixture to one of a mouth of a subject, a nose of the subject, or both the mouth and the nose of the subject for inhalation by the subject.

11. The apparatus of claim 10, wherein the first gas comprises a first predetermined percentage of the $N_2O$ in the range of 0.1% to 100% by volume.

12. The apparatus of claim 11, wherein the first gas further comprises a second predetermined percentage of a second additive in the range of 0.1% to 99.9% by volume.

13. The apparatus of claim 10, wherein the mixture comprises a predetermined percentage of the $N_2O$ in the range of 20% to 99% by volume.

14. The apparatus of claim 10, wherein the first gas further comprises one of compressed air, pure oxygen ($O_2$), air, or atmospheric air.

15. The apparatus of claim 14, wherein:
the first additive comprises one of water ($H_2O$), hydrogen peroxide ($H_2O_2$), a *cannabis* extract, an essential oil, an herbal extract, a supplement, a medication, a vitamin, caffeine, a silver, a flavoring, a nano-capacitor, or a nutrient;
the second reservoir is further configured to store a second additive;
the second additive comprises one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient; and
the second additive is different from the first additive.

16. The apparatus of claim 10, wherein the first additive comprises one of water ($H_2O$), hydrogen peroxide ($H_2O_2$), a *cannabis* extract, an essential oil, an herbal extract, a supplement, a medication, a vitamin, caffeine, a silver, a flavoring, a nano-capacitor, or a nutrient.

17. The apparatus of claim 16, wherein:
the second reservoir is further configured to store a second additive;
the second additive comprises one of the compressed air, the $O_2$, the air, the atmospheric air, the $H_2O$, the $H_2O_2$, the *cannabis* extract, the essential oil, the herbal extract, the supplement, the medication, the vitamin, the caffeine, the silver, the flavoring, the nano-capacitor, or the nutrient; and
the second additive is different from the first additive.

18. The apparatus of claim 10, wherein both the first reservoir and the second reservoir are detachably coupleable to the mask.

19. The apparatus of claim 10, wherein:
the first reservoir is detachably coupleable to the mask; and
the second reservoir is coupled to the mask.

20. The apparatus of claim 10, wherein:
the second reservoir is detachably coupleable to the mask; and
the first reservoir is coupled to the mask.

* * * * *